(12) United States Patent
Chien et al.

(10) Patent No.: US 10,010,602 B2
(45) Date of Patent: Jul. 3, 2018

(54) VACCINE COMPOSITIONS AGAINST PORCINE REPRODUCTIVE AND RESPIRATORY SYNDROME AND PORCINE CIRCOVIRUS ASSOCIATED DISEASES

(71) Applicant: Reber Genetics Co., Ltd., Taipei (TW)

(72) Inventors: Yu-Hsin Chien, Taipei (TW); Meng-Ju Tsai, Taipei (TW); Pao-Yen Lai, Taipei (TW); Wei-I Chou, Taipei (TW); Hsiu-Kang Chang, Taipei (TW)

(73) Assignee: REBER GENETICS CO., LTD., Taipei (TW)

( * ) Notice: Subject to any disclaimer, the term of this patent is extended or adjusted under 35 U.S.C. 154(b) by 23 days.

(21) Appl. No.: 15/167,911

(22) Filed: May 27, 2016

(65) Prior Publication Data

US 2016/0346377 A1  Dec. 1, 2016

Related U.S. Application Data

(60) Provisional application No. 62/169,205, filed on Jun. 1, 2015.

(51) Int. Cl.

| | |
|---|---|
| *A61K 39/12* | (2006.01) |
| *C07K 14/005* | (2006.01) |
| *C07K 14/21* | (2006.01) |
| *A61K 39/00* | (2006.01) |

(52) U.S. Cl.
CPC ............ *A61K 39/12* (2013.01); *C07K 14/005* (2013.01); *C07K 14/21* (2013.01); *A61K 2039/70* (2013.01); *C07K 2319/04* (2013.01); *C07K 2319/095* (2013.01); *C07K 2319/55* (2013.01); *C07K 2319/74* (2013.01); *C12N 2750/10022* (2013.01); *C12N 2750/10034* (2013.01); *C12N 2770/10022* (2013.01); *C12N 2770/10034* (2013.01)

(58) Field of Classification Search
None
See application file for complete search history.

(56) References Cited

U.S. PATENT DOCUMENTS

| | | | |
|---|---|---|---|
| 7,314,632 B1 | 1/2008 | Fitzgerald | |
| 7,335,361 B2 | 2/2008 | Liao et al. | |
| 7,465,455 B2* | 12/2008 | Chang | A61K 39/12 424/204.1 |
| 7,595,054 B2* | 9/2009 | Liao | A61K 39/12 424/186.1 |
| 7,596,054 B2 | 9/2009 | Liao et al. | |
| 9,339,536 B2* | 5/2016 | Chou | A61K 39/21 |
| 9,481,714 B2* | 11/2016 | Wu | A61K 39/21 |
| 9,676,826 B2* | 6/2017 | Chou | A61K 39/21 |
| 9,676,827 B2* | 6/2017 | Wu | A61K 39/21 |

FOREIGN PATENT DOCUMENTS

| | | | |
|---|---|---|---|
| WO | WO2006125076 | * | 11/2006 |
| WO | WO2014089036 | * | 6/2014 |

OTHER PUBLICATIONS

GenBank Accession No. AGJ72907 (Apr. 21, 2013) (Year: 2013).*
D. Craig Hooper et al. "Rabies ribonucleocapsid as an oral immunogen and immunological enhancer" Proc. Nati. Acad. Sci. USA, vol. 91, pp. 10908-10912, Nov. 1994, Immunology.

* cited by examiner

*Primary Examiner* — Nicole Kinsey White
(74) *Attorney, Agent, or Firm* — Hsiu-Ming Saunders; Intellectual Property Connections, Inc.

(57) ABSTRACT

A fusion protein comprising an antigen-presenting cell (APC)-binding domain or a CD91 receptor-binding domain, a translocation peptide, a fusion antigen, an endoplasmic reticulum retention sequence, and optionally a nuclear export signal is disclosed. The fusion antigen comprises a porcine reproductive and respiratory syndrome virus (PRRSV) ORF7 antigen, a PRRSV ORF1b antigen, a PRRSV ORF6 antigen, and a PRRSV ORF5 antigen. The fusion protein is useful for inducing antigen-specific cell-mediated and humoral responses.

20 Claims, 3 Drawing Sheets

PRRSFREE

PE-DRMP-NESK (PRRSFREE 4-in-1)

PE-PCV2-NESK

SEQUENCE LISTING

```
<160> NUMBER OF SEQ ID NOS: 53

<210> SEQ ID NO 1
<211> LENGTH: 252
<212> TYPE: PRT
<213> ORGANISM: Pseudomonas aeruginosa

<400> SEQUENCE: 1

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
                20                  25                  30

Ala Ile Ala Asp Thr Asn Gly Gln Gly Val Leu His Tyr Ser Met Val
            35                  40                  45

Leu Glu Gly Gly Asn Asp Ala Leu Lys Leu Ala Ile Asp Asn Ala Leu
        50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
                100                 105                 110

Ile Lys Val Phe Ile His Glu Leu Asn Ala Gly Asn Gln Leu Ser His
            115                 120                 125
```

```
Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu
                245                 250
```

<210> SEQ ID NO 2
<211> LENGTH: 61
<212> TYPE: PRT
<213> ORGANISM: Pseudomonas aeruginosa

<400> SEQUENCE: 2

```
Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg
    50                  55                  60
```

<210> SEQ ID NO 3
<211> LENGTH: 46
<212> TYPE: PRT
<213> ORGANISM: Pseudomonas aeruginosa

<400> SEQUENCE: 3

```
Pro Leu Glu Thr Phe Thr Arg His Arg Gln Pro Arg Gly Trp Glu Gln
1               5                   10                  15

Leu Glu Gln Cys Gly Tyr Pro Val Gln Arg Leu Val Ala Leu Tyr Leu
            20                  25                  30

Ala Ala Arg Leu Ser Trp Asn Gln Val Asp Gln Val Ile Arg
        35                  40                  45
```

<210> SEQ ID NO 4
<211> LENGTH: 34
<212> TYPE: PRT
<213> ORGANISM: Pseudomonas aeruginosa

<400> SEQUENCE: 4

```
Gly Trp Glu Gln Leu Glu Gln Cys Gly Tyr Pro Val Gln Arg Leu Val
1               5                   10                  15

Ala Leu Tyr Leu Ala Ala Arg Leu Ser Trp Asn Gln Val Asp Gln Val
            20                  25                  30

Ile Arg
```

<210> SEQ ID NO 5
<211> LENGTH: 313
<212> TYPE: PRT
<213> ORGANISM: Pseudomonas aeruginosa

<400> SEQUENCE: 5

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg
305                 310

<210> SEQ ID NO 6
<211> LENGTH: 112
<212> TYPE: PRT
<213> ORGANISM: Pseudomonas aeruginosa

<400> SEQUENCE: 6

```
Gly Gly Ser Leu Ala Ala Leu Thr Ala His Gln Ala Cys His Leu Pro
1               5                   10                  15
Leu Glu Thr Phe Thr Arg His Arg Gln Pro Arg Gly Trp Glu Gln Leu
                20                  25                  30
Glu Gln Cys Gly Tyr Pro Val Gln Arg Leu Val Ala Leu Tyr Leu Ala
            35                  40                  45
Ala Arg Leu Ser Trp Asn Gln Val Asp Gln Val Ile Arg Asn Ala Leu
        50                  55                  60
Ala Ser Pro Gly Ser Gly Gly Asp Leu Gly Glu Ala Ile Arg Glu Gln
65                  70                  75                  80
Pro Glu Gln Ala Arg Leu Ala Leu Thr Leu Ala Ala Ala Glu Ser Glu
                85                  90                  95
Arg Phe Val Arg Gln Gly Thr Gly Asn Asp Glu Ala Gly Ala Ala Asn
            100                 105                 110
```

<210> SEQ ID NO 7
<211> LENGTH: 407
<212> TYPE: PRT
<213> ORGANISM: Pseudomonas aeruginosa

<400> SEQUENCE: 7

```
Ala Glu Glu Ala Phe Asp Leu Trp Asn Glu Cys Ala Lys Ala Cys Val
1               5                   10                  15
Leu Asp Leu Lys Asp Gly Val Arg Ser Ser Arg Met Ser Val Asp Pro
                20                  25                  30
Ala Ile Ala Asp Thr Asn Gly Gln Gly Val Leu His Tyr Ser Met Val
            35                  40                  45
Leu Glu Gly Gly Asn Asp Ala Leu Lys Leu Ala Ile Asp Asn Ala Leu
        50                  55                  60
Ser Ile Thr Ser Asp Gly Leu Thr Ile Arg Leu Glu Gly Gly Val Glu
65                  70                  75                  80
Pro Asn Lys Pro Val Arg Tyr Ser Tyr Thr Arg Gln Ala Arg Gly Ser
                85                  90                  95
Trp Ser Leu Asn Trp Leu Val Pro Ile Gly His Glu Lys Pro Ser Asn
            100                 105                 110
Ile Lys Val Phe Ile His Glu Leu Asn Ala Gly Asn Gln Leu Ser His
            115                 120                 125
Met Ser Pro Ile Tyr Thr Ile Glu Met Gly Asp Glu Leu Leu Ala Lys
        130                 135                 140
Leu Ala Arg Asp Ala Thr Phe Phe Val Arg Ala His Glu Ser Asn Glu
145                 150                 155                 160
Met Gln Pro Thr Leu Ala Ile Ser His Ala Gly Val Ser Val Val Met
                165                 170                 175
Ala Gln Thr Gln Pro Arg Arg Glu Lys Arg Trp Ser Glu Trp Ala Ser
            180                 185                 190
Gly Lys Val Leu Cys Leu Leu Asp Pro Leu Asp Gly Val Tyr Asn Tyr
        195                 200                 205
Leu Ala Gln Gln Arg Cys Asn Leu Asp Asp Thr Trp Glu Gly Lys Ile
    210                 215                 220
Tyr Arg Val Leu Ala Gly Asn Pro Ala Lys His Asp Leu Asp Ile Lys
225                 230                 235                 240
Pro Thr Val Ile Ser His Arg Leu His Phe Pro Glu Gly Gly Ser Leu
                245                 250                 255
```

-continued

```
Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val
                405

<210> SEQ ID NO 8
<211> LENGTH: 104
<212> TYPE: PRT
<213> ORGANISM: Homo sapiens

<400> SEQUENCE: 8

Ala Glu Phe Glu Glu Pro Arg Val Ile Asp Leu Trp Asp Leu Ala Gln
1               5                   10                  15

Ser Ala Asn Leu Thr Asp Lys Glu Leu Glu Ala Phe Arg Glu Glu Leu
            20                  25                  30

Lys His Phe Glu Ala Lys Ile Glu Lys His Asn His Tyr Gln Lys Gln
        35                  40                  45

Leu Glu Ile Ala His Glu Lys Leu Arg His Ala Glu Ser Val Gly Asp
    50                  55                  60

Gly Glu Arg Val Ser Arg Ser Arg Glu Lys His Ala Leu Leu Glu Gly
65                  70                  75                  80

Arg Thr Lys Glu Leu Gly Tyr Thr Val Lys Lys His Leu Gln Asp Leu
                85                  90                  95

Ser Gly Arg Ile Ser Arg Ala Arg
            100

<210> SEQ ID NO 9
<211> LENGTH: 153
<212> TYPE: PRT
<213> ORGANISM: Artificial Sequence
<220> FEATURE:
<223> OTHER INFORMATION: A2M Minimum

<400> SEQUENCE: 9

Val Tyr Leu Gln Thr Ser Leu Lys Tyr Asn Ile Leu Pro Glu Lys Glu
1               5                   10                  15

Glu Phe Pro Phe Ala Leu Gly Val Gln Thr Leu Pro Gln Thr Cys Asp
            20                  25                  30

Glu Pro Lys Ala His Thr Ser Phe Gln Ile Ser Leu Ser Val Ser Tyr
        35                  40                  45
```

```
Thr Gly Ser Arg Ser Ala Ser Asn Met Ala Ile Val Asp Val Lys Met
 50                  55                  60

Val Ser Gly Phe Ile Pro Leu Lys Pro Thr Val Lys Met Leu Glu Arg
 65                  70                  75                  80

Ser Asn His Val Ser Arg Thr Glu Val Ser Asn His Val Leu Ile
                 85                  90                  95

Tyr Leu Asp Lys Val Ser Asn Gln Thr Leu Ser Leu Phe Phe Thr Val
                100                 105                 110

Leu Gln Asp Val Pro Val Arg Asp Leu Lys Pro Ala Ile Val Lys Val
                115                 120                 125

Tyr Asp Tyr Tyr Glu Thr Asp Glu Phe Ala Ile Ala Glu Tyr Asn Ala
            130                 135                 140

Pro Cys Ser Lys Asp Leu Gly Asn Ala
145                 150
```

<210> SEQ ID NO 10
<211> LENGTH: 24
<212> TYPE: PRT
<213> ORGANISM: Artificial Sequence
<220> FEATURE:
<223> OTHER INFORMATION: HIV-Tat Minimum

<400> SEQUENCE: 10

```
Arg Gly Asp Pro Thr Gly Gln Glu Glu Ser Lys Glu Lys Val Glu Lys
  1               5                  10                  15

Glu Thr Val Val Asp Pro Val Thr
                 20
```

<210> SEQ ID NO 11
<211> LENGTH: 641
<212> TYPE: PRT
<213> ORGANISM: Artificial Sequence
<220> FEATURE:
<223> OTHER INFORMATION: HSPs Minimum

<400> SEQUENCE: 11

```
Met Ala Lys Ala Ala Ala Ile Gly Ile Asp Leu Gly Thr Thr Tyr Ser
  1               5                  10                  15

Cys Val Gly Val Phe Gln His Gly Lys Val Glu Ile Ile Ala Asn Asp
                 20                  25                  30

Gln Gly Asn Arg Thr Thr Pro Ser Tyr Val Ala Phe Thr Asp Thr Glu
             35                  40                  45

Arg Leu Ile Gly Asp Ala Ala Lys Asn Gln Val Ala Leu Asn Pro Gln
 50                  55                  60

Asn Thr Val Phe Asp Ala Lys Arg Leu Ile Gly Arg Lys Phe Gly Asp
 65                  70                  75                  80

Pro Val Val Gln Ser Asp Met Lys His Trp Pro Phe Gln Val Ile Asn
                 85                  90                  95

Asp Gly Asp Lys Pro Lys Val Gln Val Ser Tyr Lys Gly Glu Thr Lys
                100                 105                 110

Ala Phe Tyr Pro Glu Glu Ile Ser Ser Met Val Leu Thr Lys Met Lys
            115                 120                 125

Glu Ile Ala Glu Ala Tyr Leu Gly Tyr Pro Val Thr Asn Ala Val Ile
            130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175
```

-continued

```
Thr Ala Ala Ala Ile Ala Tyr Gly Leu Asp Arg Thr Gly Lys Gly Glu
                180                 185                 190

Arg Asn Val Leu Ile Phe Asp Leu Gly Gly Thr Phe Asp Val Ser
        195                 200                 205

Ile Leu Thr Ile Asp Asp Gly Ile Phe Glu Val Lys Ala Thr Ala Gly
        210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
                260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
        290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
        340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
        370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
        420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Arg Phe Glu Leu Ser Gly Ile
450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
        500                 505                 510

Glu Glu Ile Glu Arg Met Val Gln Glu Ala Lys Tyr Lys Ala Glu
        515                 520                 525

Asp Glu Val Gln Arg Glu Arg Val Ser Ala Lys Asn Ala Leu Glu Ser
        530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Val Leu Asp Lys Cys Gln Glu
                565                 570                 575

Val Ile Ser Trp Leu Asp Ala Asn Thr Leu Ala Glu Lys Asp Glu Phe
        580                 585                 590
```

```
Glu His Lys Arg Lys Glu Leu Glu Gln Val Cys Asn Pro Ile Ile Ser
        595                 600                 605

Gly Leu Tyr Gln Gly Ala Gly Gly Pro Gly Pro Gly Gly Phe Gly Ala
    610                 615                 620

Gln Gly Pro Lys Gly Gly Ser Gly Ser Gly Pro Thr Ile Glu Glu Val
625                 630                 635                 640

Asp

<210> SEQ ID NO 12
<211> LENGTH: 15
<212> TYPE: PRT
<213> ORGANISM: Artificial Sequence
<220> FEATURE:
<223> OTHER INFORMATION: NESK

<400> SEQUENCE: 12

Leu Gln Lys Lys Leu Glu Glu Leu Glu Leu Ala Lys Asp Glu Leu
1               5                   10                  15

<210> SEQ ID NO 13
<211> LENGTH: 11
<212> TYPE: PRT
<213> ORGANISM: Artificial Sequence
<220> FEATURE:
<223> OTHER INFORMATION: NES consensus sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 13

Leu Xaa Xaa Lys Leu Xaa Xaa Leu Xaa Leu Xaa
1               5                   10

<210> SEQ ID NO 14
<211> LENGTH: 11
<212> TYPE: PRT
<213> ORGANISM: Artificial Sequence
<220> FEATURE:
<223> OTHER INFORMATION: NES C'-terminal is Ala

<400> SEQUENCE: 14

Leu Gln Lys Lys Leu Glu Glu Leu Glu Leu Ala
1               5                   10

<210> SEQ ID NO 15
<211> LENGTH: 4
<212> TYPE: PRT
<213> ORGANISM: Artificial Sequence
<220> FEATURE:
<223> OTHER INFORMATION: ER retention sequence

<400> SEQUENCE: 15

Lys Asp Glu Leu
1
```

<210> SEQ ID NO 16
<211> LENGTH: 12
<212> TYPE: PRT
<213> ORGANISM: Artificial Sequence
<220> FEATURE:
<223> OTHER INFORMATION: ER retention sequence

<400> SEQUENCE: 16

Lys Asp Glu Leu Lys Asp Glu Leu Lys Asp Glu Leu
1               5                   10

<210> SEQ ID NO 17
<211> LENGTH: 12
<212> TYPE: PRT
<213> ORGANISM: Artificial Sequence
<220> FEATURE:
<223> OTHER INFORMATION: ER retention sequence

<400> SEQUENCE: 17

Lys Lys Asp Leu Arg Asp Glu Leu Lys Asp Glu Leu
1               5                   10

<210> SEQ ID NO 18
<211> LENGTH: 13
<212> TYPE: PRT
<213> ORGANISM: Artificial Sequence
<220> FEATURE:
<223> OTHER INFORMATION: ER retention sequence

<400> SEQUENCE: 18

Lys Lys Asp Glu Leu Arg Asp Glu Leu Lys Asp Glu Leu
1               5                   10

<210> SEQ ID NO 19
<211> LENGTH: 13
<212> TYPE: PRT
<213> ORGANISM: Artificial Sequence
<220> FEATURE:
<223> OTHER INFORMATION: ER retention sequence

<400> SEQUENCE: 19

Lys Lys Asp Glu Leu Arg Val Glu Leu Lys Asp Glu Leu
1               5                   10

<210> SEQ ID NO 20
<211> LENGTH: 192
<212> TYPE: PRT
<213> ORGANISM: Artificial Sequence
<220> FEATURE:
<223> OTHER INFORMATION: truncated PCV2 ORF2

<400> SEQUENCE: 20

Asn Gly Ile Phe Asn Thr Arg Leu Ser Arg Thr Phe Gly Tyr Thr Ile
1               5                   10                  15

Lys Arg Thr Thr Val Lys Thr Pro Ser Trp Ala Val Asp Met Met Arg
            20                  25                  30

Phe Asn Ile Asn Asp Phe Leu Pro Pro Gly Gly Gly Ser Asn Pro Arg
        35                  40                  45

Ser Val Pro Phe Glu Tyr Tyr Ser Ile Ser Lys Val Lys Val Glu Phe
    50                  55                  60

Trp Pro Cys Ser Pro Ile Thr Gln Gly Asp Ser Gly Val Gly Ser Ser
65                  70                  75                  80

Ala Val Ile Leu Asp Asp Asn Phe Val Thr Lys Ala Thr Ala Leu Thr
                85                  90                  95

```
Tyr Asp Pro Tyr Val Asn Tyr Ser Ser Arg His Thr Ile Thr Gln Pro
            100                 105                 110

Phe Ser Tyr His Ser Arg Tyr Phe Thr Pro Lys Pro Val Leu Asp Ser
        115                 120                 125

Gly Gly Gly Ala Ala Pro Asn Asn Lys Arg Asn Gln Leu Trp Leu
    130                 135                 140

Arg Leu Gln Thr Ala Gly Asn Val Asp His Val Gly Leu Gly Thr Ala
145                 150                 155                 160

Phe Glu Asn Ser Ile Tyr Asp Gln Glu Tyr Asn Ile Arg Val Thr Met
                165                 170                 175

Tyr Val Gln Phe Arg Glu Phe Asn Leu Lys Asp Pro Pro Leu Asn Pro
            180                 185                 190

<210> SEQ ID NO 21
<211> LENGTH: 613
<212> TYPE: PRT
<213> ORGANISM: Pseudomonas aeruginosa

<400> SEQUENCE: 21

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
```

```
            275                 280                 285
Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Val Arg
            340                 345                 350

Gln Gly Thr Gly Asn Asp Glu Ala Gly Ala Asn Ala Asp Val Val
                355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
                435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
                515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
                595                 600                 605

Arg Glu Asp Leu Lys
        610

<210> SEQ ID NO 22
<211> LENGTH: 220
<212> TYPE: PRT
<213> ORGANISM: Artificial Sequence
<220> FEATURE:
<223> OTHER INFORMATION: DGD (ORF7 partial fragment with a tandem repeat
      D)

<400> SEQUENCE: 22

Arg His His Phe Thr Pro Ser Glu Arg Gln Leu Cys Leu Ser Ser Ile
1               5                   10                  15
```

```
Gln Thr Ala Phe Asn Gln Gly Ala Gly Thr Cys Ile Leu Ser Asp Ser
             20                  25                  30

Gly Arg Ile Ser Tyr Thr Val Glu Phe Ser Leu Pro Thr His His Thr
         35                  40                  45

Val Arg Leu Ile Arg Val Thr Ala Pro Pro Ser Ala Leu Asp Gln Val
 50                  55                  60

Ile Arg Asn Ala Leu Ala Ser Pro Gly Ser Gly Asp Leu Gly Glu
65                   70                  75                  80

Ala Ile Arg Glu Gln Pro Glu Gln Ala Arg Leu Ala Leu Thr Leu Ala
                 85                  90                  95

Ala Ala Glu Ser Glu Arg Phe Val Arg Gln Gly Thr Gly Asn Asp Glu
            100                 105                 110

Ala Gly Ala Ala Asn Ala Asp Val Val Ser Leu Thr Cys Pro Val Ala
        115                 120                 125

Ala Gly Glu Cys Ala Gly Pro Ala Asp Ser Gly Asp Ala Leu Leu Glu
    130                 135                 140

Arg Asn Tyr Pro Thr Gly Ala Glu Phe Leu Gly Asp Gly Asp Val
145                 150                 155                 160

Arg His His Phe Thr Pro Ser Glu Arg Gln Leu Cys Leu Ser Ser Ile
                165                 170                 175

Gln Thr Ala Phe Asn Gln Gly Ala Gly Thr Cys Ile Leu Ser Asp Ser
            180                 185                 190

Gly Arg Ile Ser Tyr Thr Val Glu Phe Ser Leu Pro Thr His His Thr
        195                 200                 205

Val Arg Leu Ile Arg Val Thr Ala Pro Pro Ser Ala
    210                 215                 220

<210> SEQ ID NO 23
<211> LENGTH: 60
<212> TYPE: PRT
<213> ORGANISM: Artificial Sequence
<220> FEATURE:
<223> OTHER INFORMATION: D (ORF7 partial fragment without a tandem
      repeat D)

<400> SEQUENCE: 23

Arg His His Phe Thr Pro Ser Glu Arg Gln Leu Cys Leu Ser Ser Ile
1               5                  10                  15

Gln Thr Ala Phe Asn Gln Gly Ala Gly Thr Cys Ile Leu Ser Asp Ser
             20                  25                  30

Gly Arg Ile Ser Tyr Thr Val Glu Phe Ser Leu Pro Thr His His Thr
         35                  40                  45

Val Arg Leu Ile Arg Val Thr Ala Pro Pro Ser Ala
    50                  55                  60

<210> SEQ ID NO 24
<211> LENGTH: 62
<212> TYPE: PRT
<213> ORGANISM: Artificial Sequence
<220> FEATURE:
<223> OTHER INFORMATION: R (RSAB)

<400> SEQUENCE: 24

Met Gly Ser Leu Asp Asp Phe Cys Asn Asp Ser Thr Ala Ala Gln Lys
1               5                  10                  15

Leu Val Leu Ala Phe Ser Ile Thr Tyr Thr Pro Ile Phe Val Ala Gly
             20                  25                  30

Gly Ser Ser Ser Thr Tyr Gln Tyr Ile Tyr Asn Leu Thr Ile Cys Glu
```

```
                35                  40                  45

Leu Asn Gly Thr Asp Trp Leu Ser Asn His Phe Asp Trp Ala
     50                  55                  60

<210> SEQ ID NO 25
<211> LENGTH: 165
<212> TYPE: PRT
<213> ORGANISM: Artificial Sequence
<220> FEATURE:
<223> OTHER INFORMATION: M (M12) antigen derived from PRRSV ORF1b

<400> SEQUENCE: 25

Asn Asn Lys Glu Cys Thr Val Ala Gln Ala Leu Gly Asn Gly Asp Lys
1               5                   10                  15

Phe Arg Ala Thr Asp Lys Arg Val Val Asp Ser Leu Arg Ala Ile Cys
            20                  25                  30

Ala Asp Leu Glu Gly Ser Ser Ser Pro Leu Pro Lys Val Ala His Asn
        35                  40                  45

Leu Gly Phe Tyr Phe Ser Pro Asp Leu Thr Gln Phe Ala Lys Leu Pro
    50                  55                  60

Ile Glu Leu Ala Pro His Trp Pro Val Val Ser Thr Gln Asn Asn Glu
65                  70                  75                  80

Lys Trp Pro Asp Arg Leu Val Ala Ser Leu Arg Pro Leu Asp Lys Tyr
                85                  90                  95

Ser Arg Ala Cys Ile Gly Ala Gly Tyr Met Val Gly Pro Ser Val Phe
            100                 105                 110

Leu Gly Thr Pro Gly Val Val Ser Tyr Tyr Leu Thr Lys Phe Val Lys
        115                 120                 125

Gly Glu Ala Gln Val Leu Pro Glu Thr Val Phe Ser Thr Gly Arg Ile
    130                 135                 140

Glu Val Asp Cys Arg Glu Tyr Leu Asp Asp Arg Glu Arg Glu Val Ala
145                 150                 155                 160

Ala Ser Leu Pro His
                165

<210> SEQ ID NO 26
<211> LENGTH: 58
<212> TYPE: PRT
<213> ORGANISM: Artificial Sequence
<220> FEATURE:
<223> OTHER INFORMATION: antigen PQGAB (P)

<400> SEQUENCE: 26

Gly Ser Ser Leu Asp Asp Phe Cys Tyr Asp Ser Thr Ala Pro Gln Lys
1               5                   10                  15

Val Leu Leu Ala Phe Ser Ile Thr Tyr Ala Ser Asn Asp Ser Ser Ser
            20                  25                  30

His Leu Gln Leu Ile Tyr Asn Leu Thr Leu Cys Glu Leu Asn Gly Thr
        35                  40                  45

Asp Trp Leu Ala Asn Lys Phe Asp Trp Ala
    50                  55

<210> SEQ ID NO 27
<211> LENGTH: 841
<212> TYPE: PRT
<213> ORGANISM: Artificial Sequence
<220> FEATURE:
<223> OTHER INFORMATION: PE313-DRMP-NESK

<400> SEQUENCE: 27
```

```
Met Ala Glu Ala Phe Asp Leu Trp Asn Glu Cys Ala Lys Ala Cys
1               5                   10                  15

Val Leu Asp Leu Lys Asp Gly Val Arg Ser Ser Arg Met Ser Val Asp
                20                  25                  30

Pro Ala Ile Ala Asp Thr Asn Gly Gln Gly Val Leu His Tyr Ser Met
            35                  40                  45

Val Leu Glu Gly Gly Asn Asp Ala Leu Lys Leu Ala Ile Asp Asn Ala
50                      55                  60

Leu Ser Ile Thr Ser Asp Gly Leu Thr Ile Arg Leu Glu Gly Gly Val
65                  70                  75                  80

Glu Pro Asn Lys Pro Val Arg Tyr Ser Tyr Thr Arg Gln Ala Arg Gly
                85                  90                  95

Ser Trp Ser Leu Asn Trp Leu Val Pro Ile Gly His Glu Lys Pro Ser
            100                 105                 110

Asn Ile Lys Val Phe Ile His Glu Leu Asn Ala Gly Asn Gln Leu Ser
            115                 120                 125

His Met Ser Pro Ile Tyr Thr Ile Glu Met Gly Asp Glu Leu Leu Ala
        130                 135                 140

Lys Leu Ala Arg Asp Ala Thr Phe Phe Val Arg Ala His Glu Ser Asn
145                 150                 155                 160

Glu Met Gln Pro Thr Leu Ala Ile Ser His Ala Gly Val Ser Val Val
                165                 170                 175

Met Ala Gln Thr Gln Pro Arg Arg Glu Lys Arg Trp Ser Glu Trp Ala
            180                 185                 190

Ser Gly Lys Val Leu Cys Leu Leu Asp Pro Leu Asp Gly Val Tyr Asn
            195                 200                 205

Tyr Leu Ala Gln Gln Arg Cys Asn Leu Asp Asp Thr Trp Glu Gly Lys
210                 215                 220

Ile Tyr Arg Val Leu Ala Gly Asn Pro Ala Lys His Asp Leu Asp Ile
225                 230                 235                 240

Lys Pro Thr Val Ile Ser His Arg Leu His Phe Pro Glu Gly Gly Ser
                245                 250                 255

Leu Ala Ala Leu Thr Ala His Gln Ala Cys His Leu Pro Leu Glu Thr
            260                 265                 270

Phe Thr Arg His Arg Gln Pro Arg Gly Trp Glu Gln Leu Glu Gln Cys
            275                 280                 285

Gly Tyr Pro Val Gln Arg Leu Val Ala Leu Tyr Leu Ala Ala Arg Leu
290                 295                 300

Ser Trp Asn Gln Val Asp Gln Val Ile Arg Glu Phe Val Asp His His
305                 310                 315                 320

Phe Thr Pro Ser Glu Arg Gln Leu Cys Leu Ser Ser Ile Gln Thr Ala
                325                 330                 335

Phe Asn Gln Gly Ala Gly Thr Cys Ile Leu Ser Asp Ser Gly Arg Ile
            340                 345                 350

Ser Tyr Thr Val Glu Phe Ser Leu Pro Thr His His Thr Val Arg Leu
            355                 360                 365

Ile Arg Val Thr Ala Pro Pro Ser Ala Leu Asp Gln Val Ile Arg Asn
370                 375                 380

Ala Leu Ala Ser Pro Gly Ser Gly Gly Asp Leu Gly Glu Ala Ile Arg
385                 390                 395                 400

Glu Gln Pro Glu Gln Ala Arg Leu Ala Leu Thr Leu Ala Ala Ala Glu
                405                 410                 415
```

```
Ser Glu Arg Phe Val Arg Gln Gly Thr Gly Asn Asp Glu Ala Gly Ala
            420                 425                 430

Ala Asn Ala Asp Val Val Ser Leu Thr Cys Pro Val Ala Ala Gly Glu
            435                 440                 445

Cys Ala Gly Pro Ala Asp Ser Gly Asp Ala Leu Leu Glu Arg Asn Tyr
            450                 455                 460

Pro Thr Gly Ala Glu Phe Leu Gly Asp Gly Asp Val Arg His His
465                 470                 475                 480

Phe Thr Pro Ser Glu Arg Gln Leu Cys Leu Ser Ser Ile Gln Thr Ala
            485                 490                 495

Phe Asn Gln Gly Ala Gly Thr Cys Ile Leu Ser Asp Ser Gly Arg Ile
            500                 505                 510

Ser Tyr Thr Val Glu Phe Ser Leu Pro Thr His His Thr Val Arg Leu
            515                 520                 525

Ile Arg Val Thr Ala Pro Pro Ser Ala Met Gly Ser Leu Asp Asp Phe
            530                 535                 540

Cys Asn Asp Ser Thr Ala Ala Gln Lys Leu Val Leu Ala Phe Ser Ile
545                 550                 555                 560

Thr Tyr Thr Pro Ile Phe Val Ala Gly Gly Ser Ser Thr Tyr Gln
                    565                 570                 575

Tyr Ile Tyr Asn Leu Thr Ile Cys Glu Leu Asn Gly Thr Asp Trp Leu
            580                 585                 590

Ser Asn His Phe Asp Trp Ala Leu Asp Asn Asn Lys Glu Cys Thr Val
            595                 600                 605

Ala Gln Ala Leu Gly Asn Gly Asp Lys Phe Arg Ala Thr Asp Lys Arg
            610                 615                 620

Val Val Asp Ser Leu Arg Ala Ile Cys Ala Asp Leu Glu Gly Ser Ser
625                 630                 635                 640

Ser Pro Leu Pro Lys Val Ala His Asn Leu Gly Phe Tyr Phe Ser Pro
                    645                 650                 655

Asp Leu Thr Gln Phe Ala Lys Leu Pro Ile Glu Leu Ala Pro His Trp
            660                 665                 670

Pro Val Val Ser Thr Gln Asn Asn Glu Lys Trp Pro Asp Arg Leu Val
            675                 680                 685

Ala Ser Leu Arg Pro Leu Asp Lys Tyr Ser Arg Ala Cys Ile Gly Ala
            690                 695                 700

Gly Tyr Met Val Gly Pro Ser Val Phe Leu Gly Thr Pro Gly Val Val
705                 710                 715                 720

Ser Tyr Tyr Leu Thr Lys Phe Val Lys Gly Glu Ala Gln Val Leu Pro
                    725                 730                 735

Glu Thr Val Phe Ser Thr Gly Arg Ile Glu Val Asp Cys Arg Glu Tyr
            740                 745                 750

Leu Asp Asp Arg Glu Arg Glu Val Ala Ala Ser Leu Pro His Gly Ser
            755                 760                 765

Ser Leu Asp Asp Phe Cys Tyr Asp Ser Thr Ala Pro Gln Lys Val Leu
            770                 775                 780

Leu Ala Phe Ser Ile Thr Tyr Ala Ser Asn Asp Ser Ser Ser His Leu
785                 790                 795                 800

Gln Leu Ile Tyr Asn Leu Thr Leu Cys Glu Leu Asn Gly Thr Asp Trp
                    805                 810                 815

Leu Ala Asn Lys Phe Asp Trp Ala Leu Glu Leu Gln Lys Lys Leu Glu
            820                 825                 830

Glu Leu Glu Leu Ala Lys Asp Glu Leu
```

-continued

```
              835                 840
```

<210> SEQ ID NO 28
<211> LENGTH: 746
<212> TYPE: PRT
<213> ORGANISM: Artificial Sequence
<220> FEATURE:
<223> OTHER INFORMATION: PE313-MDPR-NESK

<400> SEQUENCE: 28

```
Met Ala Glu Glu Ala Phe Asp Leu Trp Asn Glu Cys Ala Lys Ala Cys
1               5                   10                  15

Val Leu Asp Leu Lys Asp Gly Val Arg Ser Ser Arg Met Ser Val Asp
            20                  25                  30

Pro Ala Ile Ala Asp Thr Asn Gly Gln Gly Val Leu His Tyr Ser Met
        35                  40                  45

Val Leu Glu Gly Gly Asn Asp Ala Leu Lys Leu Ala Ile Asp Asn Ala
    50                  55                  60

Leu Ser Ile Thr Ser Asp Gly Leu Thr Ile Arg Leu Glu Gly Gly Val
65                  70                  75                  80

Glu Pro Asn Lys Pro Val Arg Tyr Ser Tyr Thr Arg Gln Ala Arg Gly
                85                  90                  95

Ser Trp Ser Leu Asn Trp Leu Val Pro Ile Gly His Glu Lys Pro Ser
            100                 105                 110

Asn Ile Lys Val Phe Ile His Glu Leu Asn Ala Gly Asn Gln Leu Ser
        115                 120                 125

His Met Ser Pro Ile Tyr Thr Ile Glu Met Gly Asp Glu Leu Leu Ala
    130                 135                 140

Lys Leu Ala Arg Asp Ala Thr Phe Phe Val Arg Ala His Glu Ser Asn
145                 150                 155                 160

Glu Met Gln Pro Thr Leu Ala Ile Ser His Ala Gly Val Ser Val Val
                165                 170                 175

Met Ala Gln Thr Gln Pro Arg Arg Glu Lys Arg Trp Ser Glu Trp Ala
            180                 185                 190

Ser Gly Lys Val Leu Cys Leu Leu Asp Pro Leu Asp Gly Val Tyr Asn
        195                 200                 205

Tyr Leu Ala Gln Gln Arg Cys Asn Leu Asp Asp Thr Trp Glu Gly Lys
    210                 215                 220

Ile Tyr Arg Val Leu Ala Gly Asn Pro Ala Lys His Asp Leu Asp Ile
225                 230                 235                 240

Lys Pro Thr Val Ile Ser His Arg Leu His Phe Pro Glu Gly Gly Ser
                245                 250                 255

Leu Ala Ala Leu Thr Ala His Gln Ala Cys His Leu Pro Leu Glu Thr
            260                 265                 270

Phe Thr Arg His Arg Gln Pro Arg Gly Trp Glu Gln Leu Glu Gln Cys
        275                 280                 285

Gly Tyr Pro Val Gln Arg Leu Val Ala Leu Tyr Leu Ala Ala Arg Leu
    290                 295                 300

Ser Trp Asn Gln Val Asp Gln Val Ile Arg Glu Phe Asn Asn Lys Glu
305                 310                 315                 320

Cys Thr Val Ala Gln Ala Leu Gly Asn Gly Asp Lys Phe Arg Ala Thr
                325                 330                 335

Asp Lys Arg Val Val Asp Ser Leu Arg Ala Ile Cys Ala Asp Leu Glu
            340                 345                 350

Gly Ser Ser Ser Pro Leu Pro Lys Val Ala His Asn Leu Gly Phe Tyr
```

355                 360                 365
Phe Ser Pro Asp Leu Thr Gln Phe Ala Lys Leu Pro Ile Glu Leu Ala
    370                 375                 380

Pro His Trp Pro Val Val Ser Thr Gln Asn Asn Glu Lys Trp Pro Asp
385                 390                 395                 400

Arg Leu Val Ala Ser Leu Arg Pro Leu Asp Lys Tyr Ser Arg Ala Cys
                405                 410                 415

Ile Gly Ala Gly Tyr Met Val Gly Pro Ser Val Phe Leu Gly Thr Pro
            420                 425                 430

Gly Val Val Ser Tyr Tyr Leu Thr Lys Phe Val Lys Gly Glu Ala Gln
        435                 440                 445

Val Leu Pro Glu Thr Val Phe Ser Thr Gly Arg Ile Glu Val Asp Cys
    450                 455                 460

Arg Glu Tyr Leu Asp Asp Arg Glu Arg Glu Val Ala Ala Ser Leu Pro
465                 470                 475                 480

His Arg His Phe Thr Pro Ser Glu Arg Gln Leu Cys Leu Ser Ser
                485                 490                 495

Ile Gln Thr Ala Phe Asn Gln Gly Ala Gly Thr Cys Ile Leu Ser Asp
            500                 505                 510

Ser Gly Arg Ile Ser Tyr Thr Val Glu Phe Ser Leu Pro Thr His His
        515                 520                 525

Thr Val Arg Leu Ile Arg Val Thr Ala Pro Pro Ser Ala Arg His His
    530                 535                 540

Phe Thr Pro Ser Glu Arg Gln Leu Cys Leu Ser Ser Ile Gln Thr Ala
545                 550                 555                 560

Phe Asn Gln Gly Ala Gly Thr Cys Ile Leu Ser Asp Ser Gly Arg Ile
                565                 570                 575

Ser Tyr Thr Val Glu Phe Ser Leu Pro Thr His His Thr Val Arg Leu
            580                 585                 590

Ile Arg Val Thr Ala Pro Pro Ser Ala Leu Glu Gly Ser Gly Ser Ser
        595                 600                 605

Leu Asp Asp Phe Cys Tyr Asp Ser Thr Ala Pro Gln Lys Val Leu Leu
    610                 615                 620

Ala Phe Ser Ile Thr Tyr Ala Ser Asn Asp Ser Ser His Leu Gln
625                 630                 635                 640

Leu Ile Tyr Asn Leu Thr Leu Cys Glu Leu Asn Gly Thr Asp Trp Leu
                645                 650                 655

Ala Asn Lys Phe Asp Trp Ala His Met Val Asp Met Gly Ser Leu Asp
            660                 665                 670

Asp Phe Cys Asn Asp Ser Thr Ala Ala Gln Lys Leu Val Leu Ala Phe
        675                 680                 685

Ser Ile Thr Tyr Thr Pro Ile Phe Val Ala Gly Gly Ser Ser Ser Thr
    690                 695                 700

Tyr Gln Tyr Ile Tyr Asn Leu Thr Ile Cys Glu Leu Asn Gly Thr Asp
705                 710                 715                 720

Trp Leu Ser Asn His Phe Asp Trp Ala Leu Glu Leu Gln Lys Lys Leu
                725                 730                 735

Glu Glu Leu Glu Leu Ala Lys Asp Glu Leu
            740                 745

<210> SEQ ID NO 29
<211> LENGTH: 677
<212> TYPE: PRT
<213> ORGANISM: Artificial Sequence

<220> FEATURE:
<223> OTHER INFORMATION: RAP1-PE268-313-DRMP-K3

<400> SEQUENCE: 29

```
Met Ala Glu Phe Glu Pro Arg Val Ile Asp Leu Trp Asp Leu Ala
1               5                   10                  15

Gln Ser Ala Asn Leu Thr Asp Lys Glu Leu Gly Ala Phe Arg Glu Glu
            20                  25                  30

Leu Lys His Phe Glu Ala Lys Ile Glu Lys His Asn His Tyr Gln Lys
        35                  40                  45

Gln Leu Glu Ile Ala His Glu Lys Leu Arg His Ala Glu Ser Val Gly
    50                  55                  60

Asp Gly Glu Arg Val Ser Arg Ser Arg Glu Lys His Ala Leu Leu Glu
65                  70                  75                  80

Gly Arg Thr Lys Glu Leu Gly Tyr Thr Val Lys Lys His Leu Gln Asp
            85                  90                  95

Leu Ser Gly Arg Ile Ser Arg Ala Arg Glu Phe His Leu Pro Leu Glu
        100                 105                 110

Thr Phe Thr Arg His Arg Gln Pro Arg Gly Trp Glu Gln Leu Glu Gln
    115                 120                 125

Cys Gly Tyr Pro Val Gln Arg Leu Val Ala Leu Tyr Leu Ala Ala Arg
130                 135                 140

Leu Ser Trp Asn Gln Val Asp Gln Val Ile Arg Glu Phe His His Phe
145                 150                 155                 160

Thr Pro Ser Glu Arg Gln Leu Cys Leu Ser Ser Ile Gln Thr Ala Phe
            165                 170                 175

Asn Gln Gly Ala Gly Thr Cys Ile Leu Ser Asp Ser Gly Arg Ile Ser
        180                 185                 190

Tyr Thr Val Glu Phe Ser Leu Pro Thr His His Thr Val Arg Leu Ile
    195                 200                 205

Arg Val Thr Ala Pro Pro Ser Ala Leu Asp Gln Val Ile Arg Asn Ala
210                 215                 220

Leu Ala Ser Pro Gly Ser Gly Asp Leu Gly Glu Ala Ile Arg Glu
225                 230                 235                 240

Gln Pro Glu Gln Ala Arg Leu Ala Leu Thr Leu Ala Ala Ala Glu Ser
            245                 250                 255

Glu Arg Phe Val Arg Gln Gly Thr Gly Asn Asp Glu Ala Gly Ala Ala
        260                 265                 270

Asn Ala Asp Val Val Ser Leu Thr Cys Pro Val Ala Ala Gly Glu Cys
    275                 280                 285

Ala Gly Pro Ala Asp Ser Gly Asp Ala Leu Leu Glu Arg Asn Tyr Pro
290                 295                 300

Thr Gly Ala Glu Phe Leu Gly Asp Gly Asp Val Arg His His Phe
305                 310                 315                 320

Thr Pro Ser Glu Arg Gln Leu Cys Leu Ser Ser Ile Gln Thr Ala Phe
            325                 330                 335

Asn Gln Gly Ala Gly Thr Cys Ile Leu Ser Asp Ser Gly Arg Ile Ser
        340                 345                 350

Tyr Thr Val Glu Phe Ser Leu Pro Thr His His Thr Val Arg Leu Ile
    355                 360                 365

Arg Val Thr Ala Pro Pro Ser Ala Met Gly Ser Leu Asp Asp Phe Cys
370                 375                 380

Asn Asp Ser Thr Ala Ala Gln Lys Leu Val Leu Ala Phe Ser Ile Thr
385                 390                 395                 400
```

```
Tyr Thr Pro Ile Phe Val Ala Gly Gly Ser Ser Thr Tyr Gln Tyr
            405                 410                 415

Ile Tyr Asn Leu Thr Ile Cys Glu Leu Asn Gly Thr Asp Trp Leu Ser
            420                 425                 430

Asn His Phe Asp Trp Ala Leu Asp Asn Asn Lys Glu Cys Thr Val Ala
        435                 440                 445

Gln Ala Leu Gly Asn Gly Asp Lys Phe Arg Ala Thr Asp Lys Arg Val
    450                 455                 460

Val Asp Ser Leu Arg Ala Ile Cys Ala Asp Leu Glu Gly Ser Ser Ser
465                 470                 475                 480

Pro Leu Pro Lys Val Ala His Asn Leu Gly Phe Tyr Phe Ser Pro Asp
                485                 490                 495

Leu Thr Gln Phe Ala Lys Leu Pro Ile Glu Leu Ala Pro His Trp Pro
            500                 505                 510

Val Val Ser Thr Gln Asn Asn Glu Lys Trp Pro Asp Arg Leu Val Ala
        515                 520                 525

Ser Leu Arg Pro Leu Asp Lys Tyr Ser Arg Ala Cys Ile Gly Ala Gly
    530                 535                 540

Tyr Met Val Gly Pro Ser Val Phe Leu Gly Thr Pro Gly Val Val Ser
545                 550                 555                 560

Tyr Tyr Leu Thr Lys Phe Val Lys Gly Glu Ala Gln Val Leu Pro Glu
                565                 570                 575

Thr Val Phe Ser Thr Gly Arg Ile Glu Val Asp Cys Arg Glu Tyr Leu
            580                 585                 590

Asp Asp Arg Glu Arg Glu Val Ala Ala Ser Leu Pro His Gly Ser Ser
        595                 600                 605

Leu Asp Asp Phe Cys Tyr Asp Ser Thr Ala Pro Gln Lys Val Leu Leu
    610                 615                 620

Ala Phe Ser Ile Thr Tyr Ala Ser Asn Asp Ser Ser Ser His Leu Gln
625                 630                 635                 640

Leu Ile Tyr Asn Leu Thr Leu Cys Glu Leu Asn Gly Thr Asp Trp Leu
                645                 650                 655

Ala Asn Lys Phe Asp Trp Ala Leu Glu Lys Asp Glu Leu Lys Asp Glu
            660                 665                 670

Leu Lys Asp Glu Leu
        675

<210> SEQ ID NO 30
<211> LENGTH: 584
<212> TYPE: PRT
<213> ORGANISM: Artificial Sequence
<220> FEATURE:
<223> OTHER INFORMATION: RAP1-PE268-313-MDPR-K3

<400> SEQUENCE: 30

Met Ala Glu Phe Glu Glu Pro Arg Val Ile Asp Leu Trp Asp Leu Ala
1               5                   10                  15

Gln Ser Ala Asn Leu Thr Asp Lys Glu Leu Glu Ala Phe Arg Glu Glu
            20                  25                  30

Leu Lys His Phe Glu Ala Lys Ile Glu Lys His Asn His Tyr Gln Lys
        35                  40                  45

Gln Leu Glu Ile Ala His Glu Lys Leu Arg His Ala Glu Ser Val Gly
    50                  55                  60

Asp Gly Glu Arg Val Ser Arg Ser Arg Glu Lys His Ala Leu Leu Glu
65                  70                  75                  80
```

```
Gly Arg Thr Lys Glu Leu Gly Tyr Thr Val Lys Lys His Leu Gln Asp
                85                  90                  95

Leu Ser Gly Arg Ile Ser Arg Ala Arg Glu Phe His Leu Pro Leu Glu
            100                 105                 110

Thr Phe Thr Arg His Arg Gln Pro Arg Gly Trp Glu Gln Leu Glu Gln
        115                 120                 125

Cys Gly Tyr Pro Val Gln Arg Leu Val Ala Leu Tyr Leu Ala Ala Arg
    130                 135                 140

Leu Ser Trp Asn Gln Val Asp Gln Val Ile Arg Glu Phe Asn Asn Lys
145                 150                 155                 160

Glu Cys Thr Val Ala Gln Ala Leu Gly Asn Gly Asp Lys Phe Arg Ala
                165                 170                 175

Thr Asp Lys Arg Val Val Asp Ser Leu Arg Ala Ile Cys Ala Asp Leu
            180                 185                 190

Glu Gly Ser Ser Ser Pro Leu Pro Lys Val Ala His Asn Leu Gly Phe
        195                 200                 205

Tyr Phe Ser Pro Asp Leu Thr Gln Phe Ala Lys Leu Pro Ile Glu Leu
    210                 215                 220

Ala Pro His Trp Pro Val Val Ser Thr Gln Asn Asn Glu Lys Trp Pro
225                 230                 235                 240

Asp Arg Leu Val Ala Ser Leu Arg Pro Leu Asp Lys Tyr Ser Arg Ala
                245                 250                 255

Cys Ile Gly Ala Gly Tyr Met Val Gly Pro Ser Val Phe Leu Gly Thr
            260                 265                 270

Pro Gly Val Ser Tyr Tyr Leu Thr Lys Phe Val Lys Gly Glu Ala
        275                 280                 285

Gln Val Leu Pro Glu Thr Val Phe Ser Thr Gly Arg Ile Glu Val Asp
    290                 295                 300

Cys Arg Glu Tyr Leu Asp Asp Arg Glu Arg Glu Val Ala Ala Ser Leu
305                 310                 315                 320

Pro His Arg His His Phe Thr Pro Ser Glu Arg Gln Leu Cys Leu Ser
                325                 330                 335

Ser Ile Gln Thr Ala Phe Asn Gln Gly Ala Gly Thr Cys Ile Leu Ser
            340                 345                 350

Asp Ser Gly Arg Ile Ser Tyr Thr Val Glu Phe Ser Leu Pro Thr His
        355                 360                 365

His Thr Val Arg Leu Ile Arg Val Thr Ala Pro Pro Ser Ala Arg His
    370                 375                 380

His Phe Thr Pro Ser Glu Arg Gln Leu Cys Leu Ser Ser Ile Gln Thr
385                 390                 395                 400

Ala Phe Asn Gln Gly Ala Gly Thr Cys Ile Leu Ser Asp Ser Gly Arg
                405                 410                 415

Ile Ser Tyr Thr Val Glu Phe Ser Leu Pro Thr His His Thr Val Arg
            420                 425                 430

Leu Ile Arg Val Thr Ala Pro Pro Ser Ala Leu Glu Gly Ser Gly Ser
        435                 440                 445

Ser Leu Asp Asp Phe Cys Tyr Asp Ser Thr Ala Pro Gln Lys Val Leu
    450                 455                 460

Leu Ala Phe Ser Ile Thr Tyr Ala Ser Asn Asp Ser Ser Ser His Leu
465                 470                 475                 480

Gln Leu Ile Tyr Asn Leu Thr Leu Cys Glu Leu Asn Gly Thr Asp Trp
                485                 490                 495
```

-continued

```
Leu Ala Asn Lys Phe Asp Trp Ala His Met Val Asp Met Gly Ser Leu
                500                 505                 510

Asp Asp Phe Cys Asn Asp Ser Thr Ala Ala Gln Lys Leu Val Leu Ala
            515                 520                 525

Phe Ser Ile Thr Tyr Thr Pro Ile Phe Val Ala Gly Gly Ser Ser Ser
        530                 535                 540

Thr Tyr Gln Tyr Ile Tyr Asn Leu Thr Ile Cys Glu Leu Asn Gly Thr
545                 550                 555                 560

Asp Trp Leu Ser Asn His Phe Asp Trp Ala Leu Glu Lys Asp Glu Leu
                565                 570                 575

Lys Asp Glu Leu Lys Asp Glu Leu
                580
```

<210> SEQ ID NO 31
<211> LENGTH: 525
<212> TYPE: PRT
<213> ORGANISM: Artificial Sequence
<220> FEATURE:
<223> OTHER INFORMATION: PE313-PCV2-NESK

<400> SEQUENCE: 31

```
Met Ala Glu Glu Ala Phe Asp Leu Trp Asn Glu Cys Ala Lys Ala Cys
1               5                   10                  15

Val Leu Asp Leu Lys Asp Gly Val Arg Ser Ser Arg Met Ser Val Asp
                20                  25                  30

Pro Ala Ile Ala Asp Thr Asn Gly Gln Gly Val Leu His Tyr Ser Met
            35                  40                  45

Val Leu Glu Gly Gly Asn Asp Ala Leu Lys Leu Ala Ile Asp Asn Ala
        50                  55                  60

Leu Ser Ile Thr Ser Asp Gly Leu Thr Ile Arg Leu Glu Gly Gly Val
65                  70                  75                  80

Glu Pro Asn Lys Pro Val Arg Tyr Ser Tyr Thr Arg Gln Ala Arg Gly
                85                  90                  95

Ser Trp Ser Leu Asn Trp Leu Val Pro Ile Gly His Glu Lys Pro Ser
                100                 105                 110

Asn Ile Lys Val Phe Ile His Glu Leu Asn Ala Gly Asn Gln Leu Ser
            115                 120                 125

His Met Ser Pro Ile Tyr Thr Ile Glu Met Gly Asp Glu Leu Leu Ala
        130                 135                 140

Lys Leu Ala Arg Asp Ala Thr Phe Phe Val Arg Ala His Glu Ser Asn
145                 150                 155                 160

Glu Met Gln Pro Thr Leu Ala Ile Ser His Ala Gly Val Ser Val Val
                165                 170                 175

Met Ala Gln Thr Gln Pro Arg Arg Glu Lys Arg Trp Ser Glu Trp Ala
            180                 185                 190

Ser Gly Lys Val Leu Cys Leu Leu Asp Pro Leu Asp Gly Val Tyr Asn
        195                 200                 205

Tyr Leu Ala Gln Gln Arg Cys Asn Leu Asp Asp Thr Trp Glu Gly Lys
    210                 215                 220

Ile Tyr Arg Val Leu Ala Gly Asn Pro Ala Lys His Asp Leu Asp Ile
225                 230                 235                 240

Lys Pro Thr Val Ile Ser His Arg Leu His Phe Pro Glu Gly Gly Ser
                245                 250                 255

Leu Ala Ala Leu Thr Ala His Gln Ala Cys His Leu Pro Leu Glu Thr
            260                 265                 270
```

```
Phe Thr Arg His Arg Gln Pro Arg Gly Trp Glu Gln Leu Glu Gln Cys
            275                 280                 285

Gly Tyr Pro Val Gln Arg Leu Val Ala Leu Tyr Leu Ala Ala Arg Leu
        290                 295                 300

Ser Trp Asn Gln Val Asp Gln Val Ile Arg Glu Phe Asn Gly Ile Phe
305                 310                 315                 320

Asn Thr Arg Leu Ser Arg Thr Phe Gly Tyr Thr Ile Lys Arg Thr Thr
                325                 330                 335

Val Lys Thr Pro Ser Trp Ala Val Asp Met Met Arg Phe Asn Ile Asn
            340                 345                 350

Asp Phe Leu Pro Pro Gly Gly Ser Asn Pro Arg Ser Val Pro Phe
        355                 360                 365

Glu Tyr Tyr Ser Ile Ser Lys Val Lys Val Glu Phe Trp Pro Cys Ser
        370                 375                 380

Pro Ile Thr Gln Gly Asp Ser Gly Val Gly Ser Ser Ala Val Ile Leu
385                 390                 395                 400

Asp Asp Asn Phe Val Thr Lys Ala Thr Ala Leu Thr Tyr Asp Pro Tyr
                405                 410                 415

Val Asn Tyr Ser Ser Arg His Thr Ile Thr Gln Pro Phe Ser Tyr His
            420                 425                 430

Ser Arg Tyr Phe Thr Pro Lys Pro Val Leu Asp Ser Gly Gly Gly Ala
        435                 440                 445

Ala Ala Pro Asn Asn Lys Arg Asn Gln Leu Trp Leu Arg Leu Gln Thr
450                 455                 460

Ala Gly Asn Val Asp His Val Gly Leu Gly Thr Ala Phe Glu Asn Ser
465                 470                 475                 480

Ile Tyr Asp Gln Glu Tyr Asn Ile Arg Val Thr Met Tyr Val Gln Phe
                485                 490                 495

Arg Glu Phe Asn Leu Lys Asp Pro Pro Leu Asn Pro Leu Glu Leu Gln
            500                 505                 510

Lys Lys Leu Glu Glu Leu Glu Leu Ala Lys Asp Glu Leu
        515                 520                 525

<210> SEQ ID NO 32
<211> LENGTH: 267
<212> TYPE: PRT
<213> ORGANISM: Pseudomonas aeruginosa

<400> SEQUENCE: 32

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125
```

```
Met Ser Pro Ile Tyr Thr Ile Glu Met Gly Asp Glu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu
            260                 265

<210> SEQ ID NO 33
<211> LENGTH: 59
<212> TYPE: PRT
<213> ORGANISM: Artificial Sequence
<220> FEATURE:
<223> OTHER INFORMATION: Alternative D (ORF7 antigen, without a tandem
      repeat D)

<400> SEQUENCE: 33

His His Phe Thr Pro Ser Glu Arg Gln Leu Cys Leu Ser Ser Ile Gln
1               5                   10                  15

Thr Ala Phe Asn Gln Gly Ala Gly Thr Cys Ile Leu Ser Asp Ser Gly
            20                  25                  30

Arg Ile Ser Tyr Thr Val Glu Phe Ser Leu Pro Thr His His Thr Val
        35                  40                  45

Arg Leu Ile Arg Val Thr Ala Pro Pro Ser Ala
    50                  55

<210> SEQ ID NO 34
<211> LENGTH: 25
<212> TYPE: PRT
<213> ORGANISM: Artificial Sequence
<220> FEATURE:
<223> OTHER INFORMATION: N-terminal portion of ORF6 [from a PRRSV
      isolate in Taiwan]

<400> SEQUENCE: 34

Gly Ser Ser Leu Asp Asp Phe Cys Tyr Asp Ser Thr Ala Pro Gln Lys
1               5                   10                  15

Val Leu Leu Ala Phe Ser Ile Thr Tyr
            20                  25

<210> SEQ ID NO 35
<211> LENGTH: 33
<212> TYPE: PRT
<213> ORGANISM: Artificial Sequence
<220> FEATURE:
<223> OTHER INFORMATION: N-terminal portion of ORF5 [from a PRRSV
      isolate in Taiwan]

<400> SEQUENCE: 35
```

-continued

```
Ala Ser Asn Asp Ser Ser His Leu Gln Leu Ile Tyr Asn Leu Thr
1               5                   10                  15

Leu Cys Glu Leu Asn Gly Thr Asp Trp Leu Ala Asn Lys Phe Asp Trp
                20                  25                  30

Ala

<210> SEQ ID NO 36
<211> LENGTH: 28
<212> TYPE: PRT
<213> ORGANISM: Artificial Sequence
<220> FEATURE:
<223> OTHER INFORMATION: N-terminal portion of ORF6

<400> SEQUENCE: 36

Met Gly Ser Leu Asp Asp Phe Cys Asn Asp Ser Thr Ala Ala Gln Lys
1               5                   10                  15

Leu Val Leu Ala Phe Ser Ile Thr Tyr Thr Pro Ile
                20                  25

<210> SEQ ID NO 37
<211> LENGTH: 34
<212> TYPE: PRT
<213> ORGANISM: Artificial Sequence
<220> FEATURE:
<223> OTHER INFORMATION: N-terminal portion of ORF5

<400> SEQUENCE: 37

Phe Val Ala Gly Gly Ser Ser Ser Thr Tyr Gln Tyr Ile Tyr Asn Leu
1               5                   10                  15

Thr Ile Cys Glu Leu Asn Gly Thr Asp Trp Leu Ser Asn His Phe Asp
                20                  25                  30

Trp Ala

<210> SEQ ID NO 38
<211> LENGTH: 200
<212> TYPE: PRT
<213> ORGANISM: Porcine reproductive and respiratory syndrome virus

<400> SEQUENCE: 38

Met Arg Cys Ser His Lys Leu Gly Arg Phe Leu Thr Pro His Ser Cys
1               5                   10                  15

Phe Trp Trp Leu Phe Leu Leu Cys Thr Gly Leu Ser Trp Ser Phe Val
                20                  25                  30

Ala Gly Gly Ser Ser Ser Thr Tyr Gln Tyr Ile Tyr Asn Leu Thr Ile
            35                  40                  45

Cys Glu Leu Asn Gly Thr Asp Trp Leu Ser Asn His Phe Asp Trp Ala
        50                  55                  60

Val Glu Thr Phe Val Leu Tyr Pro Val Ala Thr His Ile Leu Ser Leu
65                  70                  75                  80

Gly Phe Leu Thr Thr Ser His Phe Phe Asp Ala Leu Gly Leu Gly Ala
                85                  90                  95

Val Ser Thr Ile Gly Phe Val Gly Gly Arg Tyr Val Leu Ser Ser Val
            100                 105                 110

Tyr Gly Ala Cys Ala Phe Ala Ala Phe Val Cys Phe Val Ile Arg Ala
        115                 120                 125

Val Lys Asn Cys Met Ala Phe Arg Tyr Ala His Thr Arg Phe Thr Asn
    130                 135                 140

Phe Ile Val Asp Asp Arg Gly Arg Ile His Arg Trp Lys Ser Pro Ile
145                 150                 155                 160
```

Val Val Glu Lys Leu Gly Lys Ala Glu Val Gly Gly Asp Leu Val Thr
                165                      170                  175

Ile Lys His Val Val Leu Glu Gly Val Lys Ala Gln Pro Leu Thr Arg
            180                      185                      190

Thr Ser Ala Glu Gln Trp Glu Ala
        195                      200

<210> SEQ ID NO 39
<211> LENGTH: 173
<212> TYPE: PRT
<213> ORGANISM: Porcine reproductive and respiratory syndrome virus

<400> SEQUENCE: 39

Met Gly Ser Leu Asp Asp Phe Cys Asn Asp Ser Thr Ala Ala Gln Lys
1               5                   10                 15

Leu Val Leu Ala Phe Ser Ile Thr Tyr Thr Pro Ile Met Ile Tyr Ala
            20                      25                    30

Leu Lys Val Ser Arg Gly Arg Leu Leu Gly Leu Leu His Ile Leu Ile
        35                      40                    45

Phe Leu Asn Cys Ser Phe Thr Phe Gly Tyr Met Thr Tyr Val Arg Phe
50                    55                    60

Gln Ser Thr Asn Arg Val Ala Leu Thr Leu Gly Ala Val Val Ala Leu
65                  70                   75                    80

Leu Trp Gly Val Tyr Ser Phe Thr Glu Ser Trp Lys Phe Val Thr Ser
                  85                      90                  95

Arg Cys Arg Leu Cys Cys Leu Gly Arg Arg Tyr Ile Leu Ala Pro Ala
            100                      105                    110

His His Val Glu Ser Ala Ala Gly Leu His Ser Ile Pro Ala Ser Gly
        115                      120                    125

Asn Arg Ala Tyr Ala Val Arg Lys Pro Gly Leu Thr Ser Val Asn Gly
        130                      135                    140

Thr Leu Val Pro Gly Leu Arg Ser Leu Val Leu Gly Gly Lys Arg Ala
145                  150                  155                    160

Val Lys Arg Gly Val Val Asn Leu Val Lys Tyr Gly Arg
            165                      170

<210> SEQ ID NO 40
<211> LENGTH: 200
<212> TYPE: PRT
<213> ORGANISM: Porcine reproductive and respiratory syndrome virus

<400> SEQUENCE: 40

Met Leu Gly Lys Cys Leu Thr Ala Gly Cys Cys Ser Arg Leu Leu Phe
1               5                   10                 15

Leu Trp Cys Thr Val Pro Ser Cys Phe Val Ala Leu Val Gly Ala Ser
            20                      25                    30

Asn Ser Ser Ser Tyr Ser Gln Leu Ile Tyr Asn Leu Thr Leu Cys
        35                      40                    45

Glu Leu Asn Gly Thr Asp Trp Leu Ala Asn Lys Phe Asp Trp Ala Val
50                    55                    60

Glu Thr Phe Val Ile Phe Pro Val Leu Thr His Ile Val Ser Tyr Gly
65                  70                   75                    80

Ala Leu Thr Thr Ser His Phe Leu Asp Thr Val Gly Leu Ile Thr Val
                  85                      90                  95

Ser Thr Ala Gly Phe Tyr His Gly Arg Tyr Val Leu Ser Ser Ile Tyr
            100                      105                    110

-continued

```
Ala Thr Cys Ala Leu Ala Ala Leu Ile Cys Phe Val Ile Arg Leu Ala
            115                 120                 125

Lys Asn Cys Met Ser Trp Arg Tyr Ser Cys Thr Arg Tyr Thr Asn Phe
130                 135                 140

Leu Leu Asp Thr Lys Gly Arg Ile Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Ala Ala Thr Pro Val Thr Lys Ile
            180                 185                 190

Ser Ala Glu Gln Trp Gly Arg Pro
            195                 200

<210> SEQ ID NO 41
<211> LENGTH: 174
<212> TYPE: PRT
<213> ORGANISM: Porcine reproductive and respiratory syndrome virus

<400> SEQUENCE: 41

Met Gly Ser Ser Leu Asp Asp Phe Cys His Asp Ser Thr Ala Pro Gln
1               5                   10                  15

Lys Val Ile Leu Ala Phe Ser Ile Thr Tyr Thr Pro Val Met Ile Tyr
            20                  25                  30

Ala Leu Lys Val Ser Arg Gly Arg Leu Leu Gly Leu Leu His Leu Leu
        35                  40                  45

Ile Phe Leu Asn Cys Ala Phe Thr Phe Gly Tyr Met Thr Phe Val His
    50                  55                  60

Phe Gln Ser Thr Asn Arg Val Ala Leu Thr Met Gly Ala Val Val Ala
65                  70                  75                  80

Leu Leu Trp Gly Val Tyr Ser Ala Ile Glu Thr Trp Arg Phe Ile Thr
                85                  90                  95

Ser Arg Cys Arg Leu Cys Leu Leu Gly Arg Lys Tyr Ile Leu Ala Pro
            100                 105                 110

Ala His His Val Glu Ser Ala Ala Gly Phe His Pro Ile Ala Ala Ser
        115                 120                 125

Asp Asn His Ala Phe Val Val Arg Arg Pro Gly Ser Thr Thr Val Asn
    130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
                165                 170

<210> SEQ ID NO 42
<211> LENGTH: 30
<212> TYPE: DNA
<213> ORGANISM: Artificial Sequence
<220> FEATURE:
<223> OTHER INFORMATION: Forward primer

<400> SEQUENCE: 42
gaattcgtcg accaccactt taccccgagt                                    30

<210> SEQ ID NO 43
<211> LENGTH: 30
<212> TYPE: DNA
<213> ORGANISM: Artificial Sequence
<220> FEATURE:
<223> OTHER INFORMATION: Reverse primer
```

<400> SEQUENCE: 43
ctcgagagcc cagtcgaatt tgttagccag                                      30

<210> SEQ ID NO 44
<211> LENGTH: 30
<212> TYPE: DNA
<213> ORGANISM: Artificial Sequence
<220> FEATURE:
<223> OTHER INFORMATION: Forward primer

<400> SEQUENCE: 44
gaattcaata acaaagaatg cacggttgct                                      30

<210> SEQ ID NO 45
<211> LENGTH: 30
<212> TYPE: DNA
<213> ORGANISM: Artificial Sequence
<220> FEATURE:
<223> OTHER INFORMATION: Reverse primer

<400> SEQUENCE: 45
ctcgagagcc cagtcaaagt ggttagacag                                      30

<210> SEQ ID NO 46
<211> LENGTH: 30
<212> TYPE: DNA
<213> ORGANISM: Artificial Sequence
<220> FEATURE:
<223> OTHER INFORMATION: Forward primer

<400> SEQUENCE: 46
gaattccacc actttacccc gagtgagcgt                                      30

<210> SEQ ID NO 47
<211> LENGTH: 30
<212> TYPE: DNA
<213> ORGANISM: Artificial Sequence
<220> FEATURE:
<223> OTHER INFORMATION: Reverse primer

<400> SEQUENCE: 47
ctcgagagcc cagtcgaatt tgttagccag                                      30

<210> SEQ ID NO 48
<211> LENGTH: 30
<212> TYPE: DNA
<213> ORGANISM: Artificial Sequence
<220> FEATURE:
<223> OTHER INFORMATION: Forward primer

<400> SEQUENCE: 48
gaattcaata acaaagaatg cacggttgct                                      30

<210> SEQ ID NO 49
<211> LENGTH: 30
<212> TYPE: DNA
<213> ORGANISM: Artificial Sequence
<220> FEATURE:
<223> OTHER INFORMATION: Reverse primer

<400> SEQUENCE: 49
ctcgagagcc cagtcaaagt ggttagacag                                      30

<210> SEQ ID NO 50

```
<211> LENGTH: 19
<212> TYPE: DNA
<213> ORGANISM: Artificial Sequence
<220> FEATURE:
<223> OTHER INFORMATION: Forward primer

<400> SEQUENCE: 50
gaattcaatg gcattttca                                                    19

<210> SEQ ID NO 51
<211> LENGTH: 18
<212> TYPE: DNA
<213> ORGANISM: Artificial Sequence
<220> FEATURE:
<223> OTHER INFORMATION: Reverse primer

<400> SEQUENCE: 51 ctcgagggggg ttcaaggg                                                    18

<210> SEQ ID NO 52
<211> LENGTH: 1518
<212> TYPE: DNA
<213> ORGANISM: Artificial Sequence
<220> FEATURE:
<223> OTHER INFORMATION: DRMP coding seqeunce

<400> SEQUENCE: 52
caccacttta ccccgagtga gcgtcaattg tgtttgtcgt caatccagac tgcctttaat      60
caaggcgctg gtacttgcat cctgtcagat tctgggcgta tcagttacac tgtggagttt     120
agtttgccta cgcatcatac tgtgcgccta atccgcgtta cagcaccacc gtcagcactc     180
gaccaggtga tccgcaacgc cctggccagc cccggcagcg gcggcgacct gggcgaagcg     240
atccgcgagc agccggagca ggcccgtctg gccctgaccc tggccgccgc cgagagcgag     300
cgcttcgtcc ggcagggcac cggcaacgac gaggccggcg cggccaacgc cgacgtggtg     360
agcctgacct gccggtcgc cgccggtgaa tgcgcgggcc cggcggacag cggcgacgcc     420
ctgctggagc gcaactatcc cactggcgcg gagttcctcg gcgacggcgg cgacgtccgt     480
caccacttta ccccgagtga gcgtcaattg tgtttgtcgt caatccagac tgcctttaat     540
caaggcgctg gtacttgcat cctgtcagat tctgggcgta tcagttacac tgtggagttt     600
agtttgccta cgcatcatac tgtgcgccta atccgcgtta cagcaccacc gtcagcaatg     660
ggtagcctgg acgactttg taacgacagc accgctgctc agaaactggt tctggctttt     720
agcatcacct acccccaat ctttgttgct ggtggtagca gcagcaccta ccagtacatc     780
tacaacctga ccatctgtga actgaacggt accgactggc tgagcaacca ctttgactgg     840
gctctcgaca taacaaaga atgcacggtt gctcaggctc tgggcaacgg ggataaattt     900
cgtgccacag acaagcgtgt tgtagattct ctccgcgcca tttgtgctga tctggaaggg     960
tcgagctctc cgctcccgaa ggtcgcacac aacttgggtt tttatttttc acctgacttg    1020
acacagtttg ccaaactccc aatagaactt gcaccacact ggccggtggt gtcaacccag    1080
aacaatgaaa agtggccgga tcgtctggtt gccagccttc gccctctcga caaatacagc    1140
cgcgcgtgca tcggtgccgg ctatatggtg ggccttcgg tgtttctggg cactccaggg    1200
gtcgtgtcat actatctcac aaagtttgtt aagggcgagg ctcaagtgct tccggaaacg    1260
gtcttcagta ccggccgaat tgaggtagac tgccgtgaat atcttgatga tcgtgagcga    1320
gaagttgctg cgtccctccc acacggtagc agcctggacg acttctgcta cgacagcacc    1380
gctccgcaga aagttctgct ggctttcagc atcacctacg cttccaacga cagcagcagc    1440
```

```
cacctgcaac tgatctacaa cctgaccctg tgcgaactga acggtaccga ctggctggct    1500
aacaaattcg actgggct                                                 1518

<210> SEQ ID NO 53
<211> LENGTH: 1239
<212> TYPE: DNA
<213> ORGANISM: Artificial Sequence
<220> FEATURE:
<223> OTHER INFORMATION: MDPR coding seqeunce

<400> SEQUENCE: 53
aataacaaag aatgcacggt tgctcaggct ctgggcaacg gggataaatt tcgtgccaca      60
gacaagcgtg ttgtagattc tctccgcgcc atttgtgctg atctggaagg gtcgagctct     120
ccgctcccga aggtcgcaca caacttgggt tttatttttt cacctgactt gacacagttt     180
gccaaactcc aatagaact tgcaccacac tggccggtgg tgtcaaccca gaacaatgaa      240
aagtggccgg atcgtctggt tgccagcctt cgccctctcg acaaatacag ccgcgcgtgc     300
atcggtgccg gctatatggt gggcccttcg gtgtttctgg gcactccagg ggtcgtgtca     360
tactatctca caaagtttgt taagggcgag gctcaagtgc ttccggaaac ggtcttcagt     420
accggccgaa ttgaggtaga ctgccgtgaa tatcttgatg atcgtgagcg agaagttgct     480
gcgtccctcc cacaccgtca ccactttacc ccgagtgagc gtcaattgtg tttgtcgtca     540
atccagactg cctttaatca aggcgctggt acttgcatcc tgtcagattc tgggcgtatc     600
agttacactg tggagtttag tttgcctacg catcatactg tgcgcctgat ccgcgttaca     660
gcaccaccgt cagcacgtca ccactttacc ccgagtgagc gtcaattgtg tttgtcgtca     720
atccagactg cctttaatca aggcgctggt acttgcatcc tgtcagattc tgggcgtatc     780
agttacactg tggagtttag tttgcctacg catcatactg tgcgcctgat ccgcgttaca     840
gcaccaccgt cagcactcga gggatccggt tcctccctgg acgacttctg ctacgactcc     900
accgctcccc agaaagttct gctggctttc tccatcacct acgcttccaa cgactcctcc     960
tcccacctgc aactgatcta caacctgacc ctgtgcgaac tgaacggtac cgactggctg    1020
gctaacaaat tcgactgggc tcatatggtc gacatgggtt ctctcgacga cttttgtaac    1080
gactctaccg ctgctcagaa actggttctg gcttttttcta tcacctacac cccaatcttt    1140
gttgctggtg gttcttcttc tacctaccag tacatctaca acctcaccat ctgtgaactc    1200
aacggtaccg actggctgtc taaccacttt gactgggct                           1239
```

VACCINE COMPOSITIONS AGAINST PORCINE REPRODUCTIVE AND RESPIRATORY SYNDROME AND PORCINE CIRCOVIRUS ASSOCIATED DISEASES

REFERENCE TO RELATED APPLICATION

The present application claims priority to U.S. Provisional Application Ser. No. 62/169,205, filed Jun. 1, 2015, which is hereby incorporated by reference in its entirety.

FIELD OF THE INVENTION

The present invention relates generally to vaccines, and more specifically to subunit vaccines.

BACKGROUND OF THE INVENTION

Viruses that infect immune cells (such as T-cell, B-cell, dendritic cell, monocyte, or macrophage) include porcine reproductive and respiratory syndrome virus (PRRSV), porcine circovirus type II (PCV2), and human immunodeficiency virus (HIV). The immune cells cannot evoke immunization responses but carry the viruses. The animals that have been infected by these viruses can be easily infected by other pathogens. Porcine reproductive and respiratory syndrome virus (PRRSV) results in high losses in animal husbandry every year. Not only swine but ducks can be infected by PRRSV as well. Generally, the animals infected by the virus have no significant symptoms, but the immunity of the infected animals is reduced. This virus infects macrophages (in the alveolar and spleen), brain microglia and monocytes, and can exist in the blood and organs of the infected animals. This leads to a decrease of weight gain and an increase in the death rate due to the secondary infection.

U.S. Pat. No. 7,595,054 discloses a fusion antigen used as a subunit vaccine, in which a single antigen moieity selected from a region of ORF1b or a region of ORF7 is fused between a *Pseudomnoas exotoxin* A polypeptide that is devoide of the cytotoxic domain III, i.e., PE (ΔIII), and an endoplasmic retiuclum retention sequence.

A vaccine composition named "PRRSFREE™" by Reber Genetics Co. Ltd. comprises four separate PRRS antigens, which are designated as D, M, R, and P, respectively. These four PRRS antigens were respectively expressed by four separate vectors using the design disclosed in U.S. Pat. No. 7,595,054, and were found effective in inducing cell-mediated and humoral immune responses in animals.

SUMMARY OF THE INVENTION

In one aspect, the invention relates to a porcine reproductive and respiratory syndrome virus (PRRSV) fusion protein comprising:
(a) an antigen-presenting cell (APC)-binding domain or a CD91 receptor-binding domain, located at the N-terminus of the fusion protein;
(b) a translocation peptide of 34-112 amino acid residues in length, comprising an amino acid sequence that is at least 90% identical to SEQ ID NO: 4, 2, 3, or 6, located at the C-terminus of the APC-binding domain or the CD91 receptor-binding domain;
(c) a fusion antigen comprising:
  (i) a porcine reproductive and respiratory syndrome virus (PRRSV) ORF7 antigen;
  (ii) a PRRSV ORF1b antigen;
  (iii) a PRRSV ORF6 antigen; and
  (iv) a PRRSV ORF5 antigen;
(d) an endoplasmic reticulum retention sequence, located at the C-terminus of the fusion protein; and
(e) optionally a nuclear export signal comprising the amino acid sequence of SEQ ID NO: 13, located between the antigens and the endoplasmic reticulum retention sequence or between the translocation peptide and the antigens;
wherein the fusion antigen does not comprise full-length ORF7, ORF6, ORF5, and ORF1b protein sequences.

In one embodiment of the invention, the ORF7 or ORF1b antigen is located N-terminal to the ORF6 antigen, and the ORF5 antigen is located C-terminal to the ORF6 antigen.

In another embodiment of the invention, the ORF6 antigen is located N-terminal to the ORF5 antigen without a bridge or a linker between the ORF6 and ORF5 antigens.

In another embodiment of the invention, the fusion antigen comprises two tandem repeats of the ORF7 antigen.

In another embodiment of the invention, the ORF5 antigen is located C-terminal to the ORF6 antigen.

In another embodiment of the invention, the ORF6 antigen comprises the N-terminal portion amino acid sequence of the PRRSV ORF6 and the ORF5 antigen comprises the N-terminal portion amino acid sequence of the PRRSV ORF5, and the fusion antigen does not comprise the C-terminal portion amino acid sequences of the ORF6 and ORF5.

In another embodiment of the invention, the ORF1b antigen comprises the C-terminal portion amino acid sequence of ORF1b NSP 10 and the N-terminal portion amino acid sequence of ORF1b NSP 11, and the fusion antigen is devoid of the N-terminal and C-terminal portion amino acid sequences of the ORF1b.

In another embodiment of the invention, the APC-binding domain or the CD91 receptor-binding domain is a polypeptide comprising an amino acid sequence that is at least 90% identical to SEQ ID NO: 1, 8, 9, 10, 11, or 32.

In another embodiment of the invention, the endoplasmic reticulum retention sequence comprises the amino acid sequence KDEL (SEQ ID NO: 15) without a tandem repeat of the amino acids KDEL with the proviso that the nuclear export signal is present.

In another embodiment of the invention, the APC-binding domain or the CD91 receptor-binding domain is a polypeptide comprising an amino acid sequence that is at least 900 identical to SEQ ID NO: 1 or 32.

In another embodiment of the invention, the nuclear export signal and the ER retention sequence forms a fusion peptide with an amino acid sequence that is at least 90% identical to SEQ ID NO: 12.

In another embodiment of the invention, the endoplasmic reticulum retention sequence comprises the amino acid sequence of SEQ ID NO: 16, 17, 18, or 19 with the proviso that the nuclear export signal is not present.

In another embodiment of the invention, the APC-binding domain or the CD91 receptor-binding domain is a polypeptide comprising an amino acid sequence that is at least 90% identical to SEQ ID NO: 8.

In another aspect, the invention relates to a composition comprising:
(i) the PRRSV fusion protein of the invention; and
(ii) a porcine circovius type 2 (PCV2) fusion protein, comprising:
  (a) an antigen-presenting cell (APC)-binding domain or a CD91 receptor-binding domain, located at the N-terminus of the fusion protein;
  (b) a translocation peptide of 34-112 amino acid residues in length, comprising an amino acid sequence that is at least 90% identical to SEQ ID NO: 4, 2, 3, or 6, located at the C-terminus of the APC-binding domain or the CD91 receptor-binding domain; and
(c) a PCV2 ORF2 antigen;
(d) an endoplasmic reticulum retention sequence, located at the C-terminus of the fusion protein; and
(e) a nuclear export signal comprising the amino acid sequence of SEQ ID NO: 13, located between the antigens and the endoplasmic reticulum retention sequence or between the translocation peptide and the antigens;

wherein the PCV2 ORF2 antigen comprises the C-terminal portion amino acid sequence of PCV2 ORF2 protein, and the PCV2 fusion protein does not comprise the N-terminal portion amino acid sequence of the PCV2 ORF2 protein.

In another embodiment of the invention, the APC-binding domain or the CD91 receptor-binding domain is free of the amino acid sequence of *Pseudomonas exotoxin* A (PE) binding domain 1.

In another embodiment of the invention, the translocation peptide has 34-46 amino acid residues in length.

In another embodiment of the invention, the translocation peptide has 34-61 amino acid residues in length.

Further in another aspect, the invention relates to a method for inducing antigen-specific cell-mediated and humoral responses, comprising administering a composition comprising a therapeutically effective amount of the fusion protein of the invention to a subject in need thereof, and thereby inducing antigen-specific cell-mediated and humoral responses.

Yet in another aspect, the invention relates to a method for inducing antigen-specific cell-mediated and humoral responses, comprising administering the composition of the invention to a subject in need thereof, and thereby inducing antigen-specific cell-mediated and humoral responses.

The fusion antigen of the invention comprises neutralization and protective epitopes on ORF7, ORF6, ORF5, and ORF1b without comprising full-length ORF7, ORF6, ORF5, and ORF1b protein sequence.

The ORF7 antigen comprises the amino acid sequence of SEQ ID NO: 33, 22, or 23.

The ORF1b antigen comprises the amino acid sequence of the C-terminal portion of ORF1b NSP 10 and the N-terminal portion of ORF1b NSP 11 and is devoid of the N-terminal and C-terminal portions of ORF1b. That is, the fusion antigen comprises the amino acid sequence of the C-terminal portion of ORF1b NSP 10 and the N-terminal portion of ORF1b NSP 11 and does not comprise the amino acid sequence of the N-terminal and C-terminal portions of ORF1b.

The ORF6 antigen comprises the N-terminal portion amino acid sequence of the PRRSV ORF6 and the ORF5 antigen comprises the N-terminal portion amino acid sequence of the PRRSV ORF5, and the fusion antigen does not comprise the C-terminal portion amino acid sequences of ORF6 and ORF5. In other words, the ORF6 antigen is selected from the N-terminal portion amino acid sequence of the PRRSV ORF6, and the ORF5 antigen is selected from the N-terminal portion amino acid sequence of the PRRSV ORF5.

In another embodiment of the invention, the N-terminal portion amino acid sequence of the PRRSV ORF6 is SEQ ID NO: 34, and the N-terminal portion amino acid sequence of the PRRSV ORF5 is 35.

Further in another embodiment of the invention, the N-terminal portion amino acid sequence of the PRRSV ORF6 is SEQ ID NO: 36, and the N-terminal portion amino acid sequence of the PRRSV ORF5 is 37.

The ORF1b antigen comprises the C-terminal portion amino acid sequence of ORF1b NSP 10 and the N-terminal portion amino acid sequence of ORF1b NSP 11, and the fusion antigen is devoid of the N-terminal and C-terminal portion amino acid sequences of the ORF1b.

In one embodiment of the invention, the ORF1b antigen has less than 200 amino acid residues in length and comprises the amino acid sequence of SEQ ID NO: 25.

In another embodiment of the invention, the ORF1b antigen comprises an amino acid sequence from amino acid residue 1046 to amino acid residue 1210 of the PRRSV ORF1b.

In one embodiment of the invention, the C-terminal amino acid of the SEQ ID NO: 13 is alanine.

These and other aspects will become apparent from the following description of the preferred embodiment taken in conjunction with the following drawings.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Figure 1A:
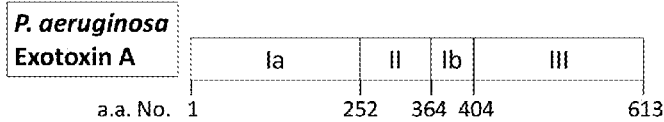
FIG. 1A is a schematic drawing showing a full-length *Pseudomonas aeruginosa* exotoxin A (PE), and partial fragment of PE.
Figure 1A:
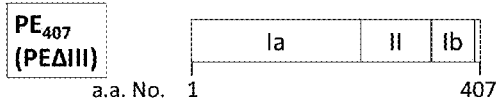
Figure 1A:
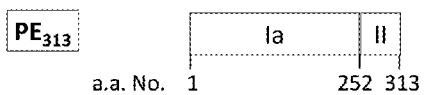
Figure 1B:
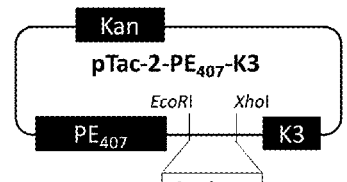
FIGS. 1B-C show vector maps.
Figure 1B:
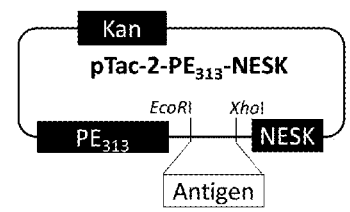
Figure 1C:
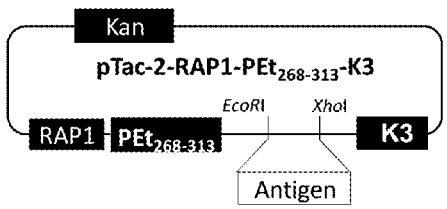
Figure 1C:
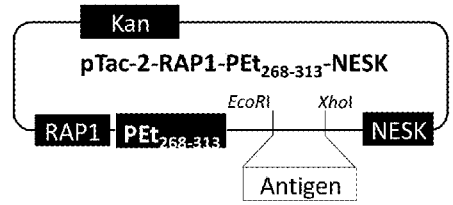

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

The term "an antigen-presenting cell (APC) or accessory cell" refers to a cell that displays foreign antigens complexed with major histocompatibility complexes (MHC's) on their surfaces. T-cells may recognize these complexes using their T-cell receptors (TCRs). These cells process antigens and present them to T-cells. Main types of professional antigen-presenting cell are dendritic cells (DCs), macrophages, which are also CD4+ and are therefore also susceptible to infection by HIV; monocytes, and certain B-cells.

The term "an antigen-presenting cell (APC)-binding domain" refers to a domain (which is a polypeptide) that can bind to an antigen-presenting cell (APC). The APC-binding domain may be a polypeptide comprising an amino acid sequence that is at least 90% identical to the sequence selected from the group consisting of SEQ ID NOs: 1 and 8-11. An APC-binding domain is a ligand that recognizes and binds to a receptor on APC.

Cluster of differentiation 91 (CD91) is a protein that forms a receptor in the membrane of cells and is involved in receptor-mediated endocytosis.

The term "$PE_t$" refers to a translocation peptide (or a translocation domain) with 34-112 amino acid residues in length. $PE_t$ may comprises the amino acid sequence that is at least 90% identical to SEQ ID NO: 2-4 and 6. For example, the amino acid sequence of $PE_t$ may be a fragment of a.a. 280-a.a. 313 (SEQ ID NO: 4), a.a. 268-a.a. 313 (SEQ ID NO: 3), a.a. 253-a.a. 313 (SEQ ID NO: 2), or a.a. 253-a.a. 364 (SEQ ID NO: 6) of PE. That is, the amino acid sequence of $PE_t$ may contain any region of the PE domain II (a.a. 253 to a.a. 364; SEQ ID NO: 6) as long as it comprises a.a. 280-a.a. 313 (SEQ ID NO: 4) essential sequence (i.e., the essential fragment).

The $PE_{407}$ (SEQ ID NO: 7) is described in prior patent (U.S. Pat. No. 7,335,361 B2) as PE(ΔIII).

The term "minimum translocation peptide" refers to $PE_{253\text{-}313}$ (SEQ ID NO: 2), which can translocate an antigen into the cytoplasm of a target cell.

The term "an endoplasmic reticulum (ER) retention sequence" refers to a peptide whose function is to assist translocation of an antigen from the cytoplasm into ER and retains the antigen in the lumen of the ER. An ER retention sequence comprises the sequence of Lys Asp Glu Leu (KDEL; SEQ ID NO: 15) or RDEL. An ER retention sequence may comprise the sequence KDEL, RDEL, KDELKDELKDEL (K3; SEQ ID NO: 16), KKDL- RDELKDEL (K3; SEQ ID NO: 17), KKDELRDELKDEL (K3; SEQ ID NO: 18), or KKDELRVELKDEL (K3; SEQ ID NO: 19).

A nuclear export signal (NES) refers to a short amino acid sequence of 4 hydrophobic residues in a protein that targets it for export from the cell nucleus to the cytoplasm through the nuclear pore complex using nuclear transport. The NES is recognized and bound by exportins. The most common spacing of the hydrophobic residues to be $L_{xx}KL_{xx}L_xL_x$ (SEQ ID NO. 13), where "L" is leucine, "K" is lysine and "x" is any naturally occurring amino acid. For example, an artificial NES may comprise the sequence Leu Gln Lys Lys Leu Glu Glu Leu Glu Leu Ala (LQKKLEELELA; SEQ ID NO: 14).

The term "NESK" refers to a fusion peptide of a NES and an ER retention signal (i.e., a NES fused to an ER retention signal). It is an artificial peptide possessing the function of a nuclear export signal (NES) and an ER retention sequence. Thus, it can export an antigen from the cell nucleus to the cytoplasm through the nuclear pore complex, and assist translocation of an antigen from the cytoplasm to ER and retain the antigen in the lumen of the ER. For example, the amino acid sequence of NESK may be LQKKLEELE-LAKDEL (SEQ ID NO: 12).

Subunit vaccines are vaccines that use only part of the disease-causing virus. This strategy is used most often when one part of the virus is responsible for creating disease. The part responsible for creating disease is a protein, which we call the antigen.

An antigen may be a pathogenic protein, polypeptide or peptide that is responsible for a disease caused by the pathogen, or is capable of inducing an immunological response in a host infected by the pathogen. The antigen may be a fusion antigen from a fusion of two or more antigens selected from one or more pathogenic proteins. For example, a fusion antigen of PRRSV ORF6 and ORF5 fragments, or a fusion of antigenic proteins from PRRSV and PCV2 pathogens.

An epitope is a part of antigen. A protective epitope means when the epitope combines with an antibody, it helps in the functioning of the antibody instead of going against it.

The presence of neutralizing or neutralization epitopes is the structural basis of prophylactic vaccines. Neutralizing epitopes are critical for viral cell attachment/entry.

As used herein, "a porcine reproductive and respiratory syndrome virus (PRRSV) ORF7 antigen" is a peptide that is selected from a portion of PRRSV ORF7 and contains protective epitopes.

As used herein, "a PRRSV ORF1b antigen" is a peptide that is selected from a portion of PRRSV ORF1b and contains protective epitopes.

As used herein, "a PRRSV ORF6 antigen" is a peptide that is selected from a portion of PRRSV ORF6 and contains protective epitopes.

As used herein, "a PRRSV ORF5 antigen" is a peptide that is selected from a portion of PRRSV ORF5 and contains protective epitopes.

The term "PRRSFREE" refers to a vaccine composition comprising the four fusion proteins $PE_{407}$-M-K3, $PE_{407}$-P-K3, $PE_{407}$-R-K3, and $PE_{407}$-D-K3.

The terms "M12" and "M" are interchangeable. The term "M12" as used herein refers to a fusion antigen from fusion of PRRSV NSP 10 (C-terminal domain sequence) and NSP 11 (N-terminal domain sequence).

The terms "PQAB" and "P" are interchangeable. The term "P" as used herein refers to a fusion antigen from fusion of the N-terminal portion of PRRSV ORF6 and the N-terminal portion of ORF5 without a bridge/linker sequence between the ORF6 and ORF5 sequences.

The terms "RSAB" and "R" are interchangeable. The term "R" as used herein refers to a fusion antigen from fusion of the N-terminal portion of PRRSV ORF6 and the N-terminal portion of ORF5 without a bridge/linker sequence between the ORF6 and ORF5 sequences.

The terms "DGD" and "D" are interchangeable. The term "D" as used herein refers to an antigen comprising two repeats of the C-terminal portion of PRRSV ORF7.

The term "treating" or "treatment" refers to administration of an effective amount of the fusion protein to a subject in need thereof, who has cancer or infection, or a symptom or predisposition toward such a disease, with the purpose of cure, alleviate, relieve, remedy, ameliorate, or prevent the disease, the symptoms of it, or the predisposition towards it. Such a subject can be identified by a health care professional based on results from any suitable diagnostic method.

The term "an effective amount" refers to the amount of an active compound that is required to confer a therapeutic effect on the treated subject. Effective doses will vary, as recognized by those skilled in the art, depending on rout of administration, excipient usage, and the possibility of co-usage with other therapeutic treatment.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Methods

Synthesis of the Fusion Antigens DRMP and MDPR

DNA sequences encoding the fusion antigens DRMP (SEQ ID NO: 52), MDPR (SEQ ID NO: 53) and PCV2 ORF2 antigen (SEQ II) NO: 20) were respectively synthesized and further cloned into the plasmids pTAC-2-$PE_{313}$-NESK or pTAC-2-RAP1-$PEt_{268-313}$-K3. All synthesized sequences were optimized for *E. coli* growth. Respective forward and reverse primers were used in PCR for DRMP or MDPR DNA amplification. The amplified DNA fragment was digested by EcoRI and XhoI, then was ligated into the indicated vector. The fusion protein $PE_{313}$-PCV2-NESK was cloned in a similar way.

Table 1 shows the sequences of the forward and reverse primers used for cloning into plasmids. Bold letters indicate EcoRI cutting site; Italic letters indicate SalI cutting site; Italic and bold letters indicate XhoI cutting site; Underlined letters indicate antigen sequence.

TABLE 1

| Plasmid | Forward primer | Reverse primer |
|---|---|---|
| For cloning DRMP into pTAC-2-$PE_{313}$-NESK | gaattc*gtcgac*caccactttaccccgagt (SEQ ID NO: 42) | *ctcgag*agcccagtcgaatttgttagccag (SEQ ID NO: 43) |
| For cloning MDPR to pTAC-2-$PE_{313}$-NESK | gaattcaataacaaagaatgcacggttgct (SEQ ID NO: 44) | *ctcgag*agcccagtcaaagtggttagacag (SEQ ID NO: 45) |
| For cloning DRMP to pTAC-2-RAP1-$PEt_{268-313}$-K3 | gaattccaccactttaccccgagtgagcgt (SEQ ID NO: 46) | *ctcgag*agcccagtcgaatttgttagccag (SEQ ID NO: 47) |
| For cloning MDPR to pTAC-2-RAP2-$PEt_{268-313}$-K3 | gaattcaataacaaagaatgcacggttgct (SEQ ID NO: 48) | *ctcgag*agcccagtcaaagtggttagacag (SEQ ID NO: 49) |
| For cloning PCV2 ORF2 to pTAC-2-$PE_{313}$-NEXK | gaattcaatggcattttca (SEQ ID NO: 50) | *ctcgag*ggggttcaaggg (SEQ ID NO: 51) |

Example 1

Construction of Expression Vectors

FIG. 1A shows PE contains 3 domains (I, II, and III). $PE_{407}$ is the region from a.a. 1 to a.a 407 of PE. $PE_{407}$ does not contain the cytotoxic domain Ill and thus contains domains I and II. $PE_{313}$ is the region from a.a. 1 to a.a. 313 of PE. Thus, $PE_{313}$ contains only domain Ia and a partial N-terminal region of domain II of PE.

FIGS. 1B-C show constructions of expression vectors, each of which comprises an antigen-presenting cell (APC)-binding domain, a translocation peptide, an antigen, with (bottom panel) or without (top panel) a nuclear export signal (NES); and an endoplasmic reticulum (ER) retention sequence (top panel, K3 or bottom panel, K), the ER retention sequence being located at the C-terminus of the fusion protein. The plasmids pTac-2-$PE_{313}$-NESK, pTac-2-$PE_{407}$-K3, pTac-2-RAP1-$PE_{268-313}$-NESK and pTac-2-RAP1-$PE_{268-313}$-K3 were generated as follows: The ${}^{NdeI}PE_{313}$-${}^{(EcoRI,\ XhoI)}$-$NESK^{XhoI}$, ${}^{NdeI}PE_{407}$-${}^{(EcoRI,\ XhoI)}$-$K3^{XhoI}$, ${}^{NdeI}RAP1$-${}^{(EcoRI)}$-$PE_{268-313}$-${}^{(EcoRI,\ XhoI)}$-$NESK^{XhoI}$ and ${}^{NdeI}RAP1$-${}^{(EcoRI)}$-$PE_{268-313}$-${}^{(EcoRI,\ XhoI)}$-$K3^{XhoI}$ fragments were synthesized by a PCR method and then ligated into a pUC18 back bond with kanamycin resistance gene to obtain respective plasmids.

A target DNA encoding an antigen or a fusion antigen of a pathogen of interest may then be inserted into the aforementioned plasmids to generate an expression vector for expression of a fusion protein. For example, a DNA fragment encoding an antigen of Porcine Circovirus Type 2 (PCV2) ORF2 (SEQ ID NO: 20) was synthesized and inserted into the plasmids pTac-2-$PE_{313}$-NESK to generate the expression vector $PE_{313}$-PCV2-NESK (FIG. 1F).

The following target DNA fragments were synthesized:

(i) a target DNA encoding an antigen comprising two repeats of the C-terminal portion of PRRSV ORF7. The antigen is designated as "DGD" or "D".

(ii) a target DNA encoding a fusion antigen from fusion of PRRSV NSP 10 (C-terminal domain sequence) and NSP 11 (N-terminal domain sequence). The antigen is designated as "M12" or "M".

(iii) a target DNA encoding a fusion antigen from fusion of the N-terminal portion of PRRSV ORF6 and the N-terminal portion of ORF5 without a bridge/linker sequence between the ORF6 and ORF5 sequences. The antigen is designated as "RSAB" or "R".

(iv) a target DNA encoding a fusion antigen from fusion of the N-terminal portion of PRRSV ORF6 and the N-terminal portion of ORF5 without a bridge/linker sequence between the ORF6 and ORF5 sequences. The antigen is designated as "PQAB" or "P".

The above target DNA fragments were inserted into the plasmid shown in FIG. 1B upper panel to generate fusion proteins $PE_{407}$-M-K3, $PE_{407}$-K3, $PE_{407}$-R-K3, and $PE_{407}$-D-K3, respectively (FIG. 1D).

A target DNA fragment encoding a fusion antigen comprising all of the four aforementioned antigens D, R, M, and P (such as DRMP, MDPR, etc.) was synthesized and inserted into the plasmids pTac-2-$PE_{313}$-NESK to generate an expression vector expressing the fusion protein PE-DRMP-NESK (FIG. 1E), which is designates as (also "PRRSFREE 4-in-1").

Example 2

Protein Expression

*E. coli* BL21 cells harboring plasmids for expression of fusion proteins were respectively cultured in Luria Bertani broth containing 25 ppm of kanamycin at 37° C. When the culture reaching early log phase, (A600=0.1 to 0.4), isopropyl-1-thio-β-D-galactopyranoside (IPTG) was added with a final concentration of 0.5 to 2 mM for induction. Cells were harvested after induction after 4 hours and immediately stored at −70° C. The fusion proteins were purified by urea extraction as described previously (Liao et al., 1995. Appl. Microbiol. Biotechnol. 43: 498-507) and then were refolded by dialysis method against 50× volume of TNE buffer (50 mM Tris, 50 mM NaCl and 1 mM EDTA) at 4° C. for overnight. The refolded proteins were subjected to SDS-PAGE analyses and quantitative analyses performed using Bradford Protein Assay Kit (Pierce). The results indicated that most of the refolded proteins were monomers under a non-reduced condition, indicating that the fusion proteins refolded easily and were not aggregated.

Example 3

PRRSV Subunit Vaccines Immunogenicity Assay

Mice were vaccinated with 200 μl PRRSV subunit vaccine containing 30 μg/shot of PRRSFREE 4-in-1 or PRRSFREE and ISA206 adjuvant via s.c. injection once a week for 2 weeks. The control group (placebo) was injected with PBS.

All mice were sacrificed 14 days after the last immunization, and the spleens were harvested. The splenocytes were isolated and cultured in 96-well plate ($10^5$ cells/100 μl/well) with or without the stimulant recombinant antigen protein at 37° C. for 72 hr. Depending on the vaccine used in immunization, the stimulant recombinant antigen protein used was PRRSFREE antigens, PRRSFREE-4-in-one chimeric fusion antigen, or PCV2 ORF2 antigen for detecting antigen-specific cell-mediated immune response. The cell culture supernatant was collected and interferon-gamma (IFN-γ) in the supernatant was determined by IFN-γ Mouse Antibody Pair (Invitrogen).

Depending on the vaccine used for immunization, PRRSFREE antigens, or PRRSFREE 4-in-one fusion antigen, or PCV2 ORF2 antigen was coated in ELISA plates for detecting humoral immune response. After coating, the plates were washed and blocked before adding diluted mice serum. Then the plates were washed, hybridized with HRP-conjugated secondary antibody followed by adding TMB substrate. After the reaction was stopped, the result was detected by ELISA reader.

Example 4

Cell-Mediated Immune Response (CMI) and Humoral Immune Response

Figure 2A:
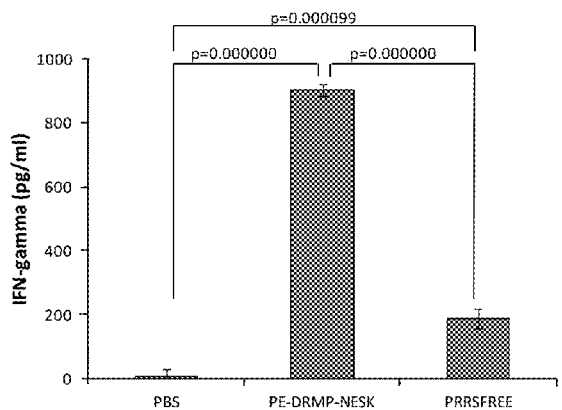
FIG. 2A is a graph showing antigen-specific cell-mediated immune (CMI) responses in mice immunized with PBS, or the vaccine composition PRRSFREE 4-in-1 or PRRSFREE.

FIG. 2A shows that the IFN-γ concentration in the vaccinated groups was higher than that in the control group, indicating that a CMI response was induced upon vaccinations. Furthermore, the IFN-γ concentration of the group receiving PRRSFREE 4-in-1 vaccine was dramatically higher than that in the PRRSFREE-treated group. The result demonstrates that PRRSFREE 4-in-1 vaccine, which was composed of one single fused antigen, can surprisingly induce a stronger CMI response than the PRRSFREE vaccines composed of four separate antigens.

Figure 2B:
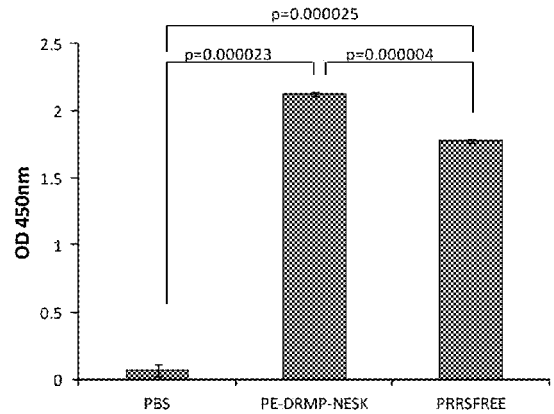
FIG. 2B is a graph showing antigen specific antibody (IgG) responses for mice immunized with PBS or PBS, or the vaccine composition PRRSFREE 4-in-1 or PRRSFREE.

FIG. 2B shows vaccine-immunized groups had higher antigen-specific antibody titers than the control group. Mice vaccinated with the PRRSFREE 4-in-1 vaccine had a higher antibody titer than the group immunized with the PRRSFREE vaccine. The result shows that PRRSFREE 4-in-1 can induce a stronger humoral immune response than the PRRSFREE vaccine.

The data in FIGS. 2A-B indicate that PRRSFREE 4-in-1, which contains a fusion protein comprising one single fusion antigen with fusion of D, M, P, and R antigens, can elicit a stronger cellular and humoral immune responses than the PRRSFREE vaccine, which contains four individual, separate antigens (i.e., the four antigens M, M, P, R are not fused) with each antigen in a respective fusion protein.

Example 5

Combination Vaccines with Porcine Cicovirus Type 2 (PCV2) ORF2 Subunit Vaccine

Figure 1D:
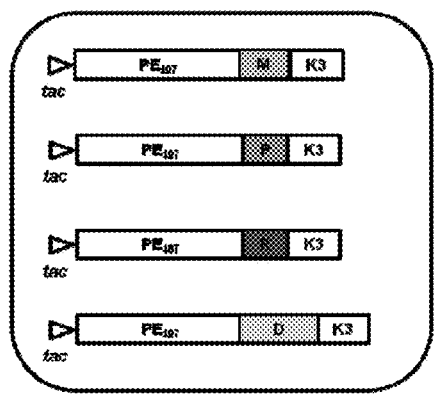
FIG. 1D is a schematic drawing showing four separate plasmids that are used for preparation of a vaccine composition that is named as PRRSFREE. The vaccine composition PRRSFEE comprises four separate, individual PE fusion proteins. Each individual PE fusion protein in the PRRSFREE vaccine composition comprises a PE($_A$III) fragment (PE$_{407}$), a single antigen moiety (designated as M, P, R, or D), and an endoplasmic retention sequence (K3). The term "D" or "DGD" represents an antigen from PRRSV nucleoprotein ORF7. The term "R" or "RSAB" represents a fusion antigen of PRRSV ORF6/Membrane protein and ORF5/major envelop protein without a bridge/linker sequence in-between. The term "M" or "M12" represents an antigen from PRRSV ORF1b, and is an artificial fusion antigen of PRRSV nonstructural proteins NSP 10 and NSP 11. The term "P" or "PQAB" represents a fusion antigen of PRRSV ORF6/Membrane protein and ORF5/major envelop protein without a bridge/linker sequence in-between. The term "PE($_A$III)" represents a PE fragment without the cytotoxic domain III. The term "PE$_{407}$" represents a *Pseudomonas exotoxin* A (PE) polypeptide from amino acid 1 to amino acid 407.
Figure 1E:
FIG. 1E is a schematic drawing showing a plasmid that is used for preparation of a PE fusion protein called PE-DRMP-NESK or PRRSFREE 4-in-one. The PE-DRMP-NESK fusion protein comprises a PE($_A$III) fragment (PE$_{313}$), a single fusion polypeptide comprising four antigen moieties (designated as DRMP), a nuclear export signal (NES), and an endoplasmic retention sequence (K).
Figure 1F:
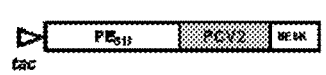
FIG. 1F is a schematic drawing showing a plasmid encoding a fusion protein comprising a PE($_A$III) fragment (PE$_{313}$), a single antigen moiety (designated as PCV2), a nuclear export signal (NES), and an endoplasmic retention sequence (K).

Mice were vaccinated with PBS, PRRSFREE 4-in-one plus PE-PCV2-NESK, or PRRSFREE plus PEI-PCV2-NESK combo vaccines according to the immunization schedule as described above. The PRRSFREE 4-in-one plus PE-PCV2-NESK combo vaccine contains PE-DRMP-NESK (FIG. 1D) and PE-PCV2-NESK (FIG. 1F) fusion proteins. The PRRSFREE plus PE-PCV2-NESK combo vaccine contains 5 separate fusion proteins: (1) PE-DGD-K3, PE-M12-K3, PE-PQAB-K3, PE-RSAB-K3 (FIG. 1D), and PE-PCV2-NESK (FIG. 1F).

Example 6

Combination Vaccines with PCV2 ORF2 Subunit Vaccine

Figure 3A:
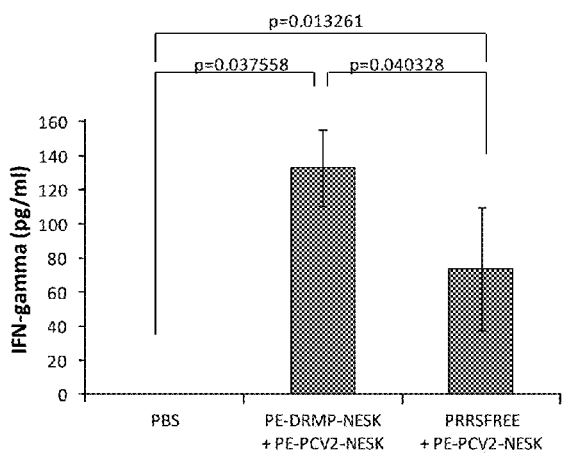
FIG. 3A is a graph showing PRRSFREE antigen specific CMI response for mice immunized with PBS or different PRRS/PCV2 combo vaccines.
Figure 3B:
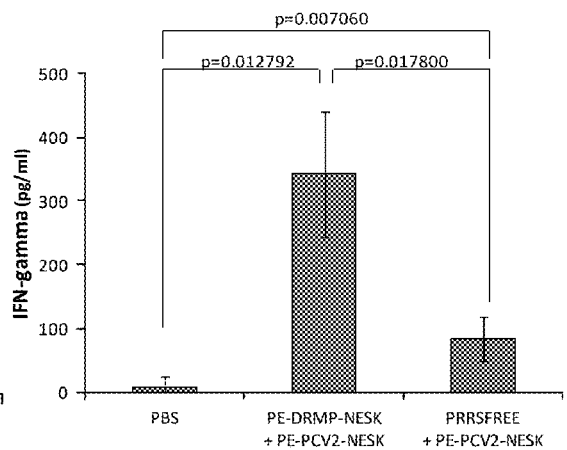
FIG. 3B is a graph showing PCV2 ORF2 antigen specific CMI response for mice immunized with PBS or different PRRS/PCV2 ORF2 combo vaccines.

FIG. 3A shows PRRSV antigen-specific (PRRSFREE 4-in-1 fusion antigen, and PRRSFREE antigens) and FIG. 3B shows PCV2-ORF2-specific CMI responses. The data indicate that the mice group immunized with the combination of PRRSFREE 4-in-1 fusion antigen and PCV2 ORF2 subunit vaccine showed a stronger CMI response than that in the mice group immunized with the combination of PRRSFREE (4 separate antigens) and PCV2 ORF2 subunit vaccine.

Figure 4A:
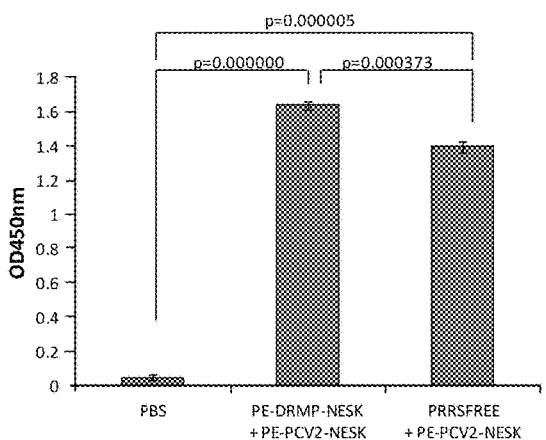
FIG. 4A is a graph showing PRRSFREE antigen specific antibody (IgG) response for mice immunized with PBS or different PRRS/PCV2 combo vaccines.

FIG. 4A shows PRRSV antigen-specific antibody responses. An ELISA method was used to measure antigen-specific antibody titers. For the group treated with the combination of PE-DRMP-NESK and PE-PCV2-NESK (i.e., two fusion proteins), the fusion antigen DRMP was used to measure the antigen-specific antibody titer. For the group treated with the combination of PRRSFREE and PE-PCV2-NESK (i.e., 5 fusion proteins), four antigens D, R, M, and P were used to measure the antigen-specific antibody titer. The data indicate that the mice group immunized with the combination of PRRSFREE 4-in-1 fusion antigen and PCV2 ORF2 subunit vaccine showed a stronger PRRSFREE 4-in-1 fusion antigen-specific humoral response than that in the mice group immunized with the combination of PRRSFREE (4 separate antigens) and PCV2 ORF2 subunit vaccine (FIG. 4A).

Figure 4B:
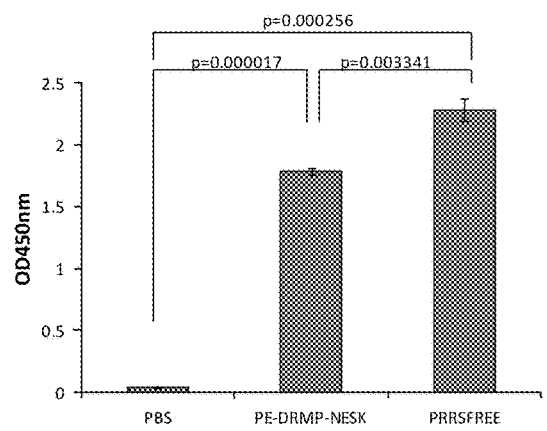
FIG. 4B is a graph showing PCV2 ORF2 antigen specific antibody (IgG) response for mice immunized with PBS or different PRRS/PCV2 combo vaccines.

FIG. 4B shows PCV2-ORF2 antigen-specific antibody responses. Surprisingly, mice immunized with the combination of PRRSFREE (4 separate antigens) and PCV2 ORF2 subunit vaccine (PE-PCV2-NESK) had a higher PCV2-specific antibody titer than the group immunized with the combination of PRRSFREE 4-in-1 fusion antigen (PE-DRMP-NESK) and PCV2 ORF2 subunit vaccine (PE-PCV2-NESK). The results indicate there was a differential PRRSV antigen-specific and PCV2-specific humoral immune responses between the two PRRSV/PCV2 combo vaccines.

It is clear that both approaches are effective in inducing CMI and humoral immune responses. The PRRSV/PCV2 combo vaccine comprising 2 fusion proteins (PE-DRMP-NESK and PE-PCV2-NESK) shows better efficacy in three out of four immune responses examined. This study demonstrates that PRRSV/PCV2 combo vaccine composed of PRRSV chimeric fusion antigen and PCV2 ORF2 antigen is a better choice than the one composed of 5 individual antigens. Nevertheless, both approaches are useful for inducing immune responses in an animal.

Example 7

Fusion of Two Antigens v. Fusion of 4 Antigens

Figure 5:
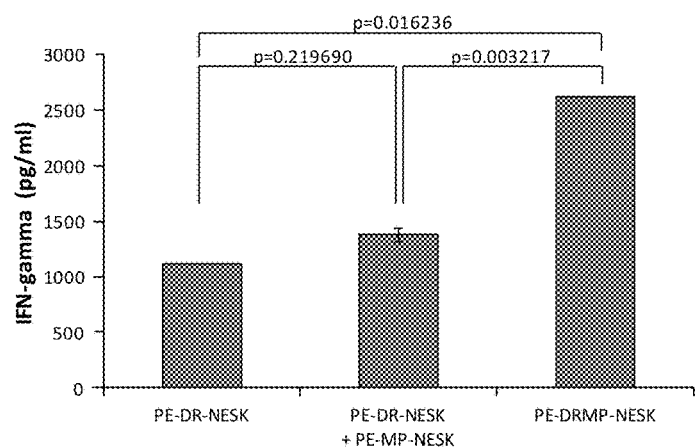
FIG. 5 is a graph showing PRRSFREE antigen specific CMI responses in mice immunized with (I) a fusion protein comprising a fusion of two antigens (a fusion of the antigens D and R in $PE_{313}$-DR-NESK), or (2) a combination of two separate fusion proteins, each fusion protein comprising a fusion of two antigens (a fusion of D and R in $PE_{313}$-DR-NESK, or a fusion of M and P in $PE_{313}$-MP-NESK), or (3) a fusion protein comprising a fusion of four antigens (a fusion of D, R, M, and P in $PE_{313}$-DRMP-NESK).

Three groups of 6-weeks-old female C57BL/6 mice (3 mice per group) were injected subcutaneously with (1) 15 µg of PE-DR-NESK protein, (2) a combination of 15 µg PE-DR-NESK and 15 µg of PE-MP-NESK proteins, or (3) 30 µg of PE-DRMP-NESK, in 200 µl of 50% ISA206 at weekly intervals three times. Mice were killed at 1 week after the last immunization, and splenocytes were harvested. Splenocytes were stimulated with 4 PRRSV antigens (M12, DgD, PQAB and RSAB, 2.5 μg/ml of each) for 72 hr, and IFN-γ in the cell-free supernatants of each group were detected using ELISA kit. FIG. 5 shows that mice immunized with PE-DRMP-NESK showed the greatest CMI response among three groups.

Example 8

Cell-Mediated Immunity in Swine

Figure 6:
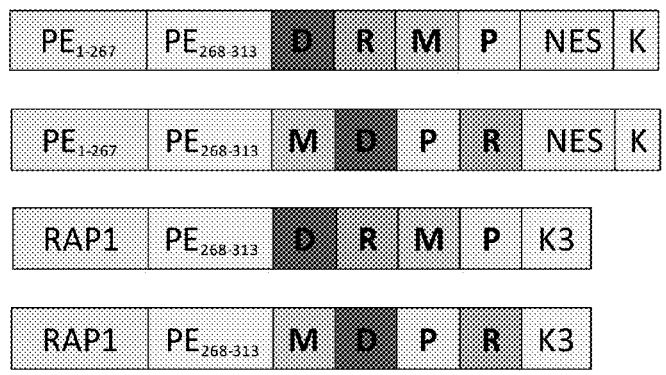
FIG. 6 is a schematic drawing showing various fusion proteins used for immunizing swine against PRRSV infection.

Five-weeks-old SPF swine (2-4 swine per group) were injected intramuscularly with one of the following vaccines: (1) PRRSFREE, (2) PE-DRMP-NESK, (3) PE-MDPR-NESK, (4) RAP1-PE$_{268-313}$-DRMP-K3, (5) RAP1-PE$_{268-313}$-MDPR-K3 in 2 ml of 50% ISA206, or (6) PBS as placebo, twice at weekly intervals. FIG. 6 shows designs of these vaccines. The antigen in each injection was 300 μg in 2 ml of 50% ISA206. Peripheral blood mononuclear cells (PBMCs) of vaccinated swine were harvested at 3 week after last immunization. Depending on the vaccine used in immunization, the PBMCs were stimulated with PRRS-FREE antigens (M12, DgD, PQAB and RSAB, 2.5 ug/ml of each), PE-DRMP-NESK, PE-MDPR-NESK, RAP1-PE$_{268-313}$-DRMP-K3, or RAP1-PE$_{268-313}$-MDPR-K3 for 72 hr, then IFN-γ in the cell-free supernatants of each group were detected using ELISA kit.

Figure 7:
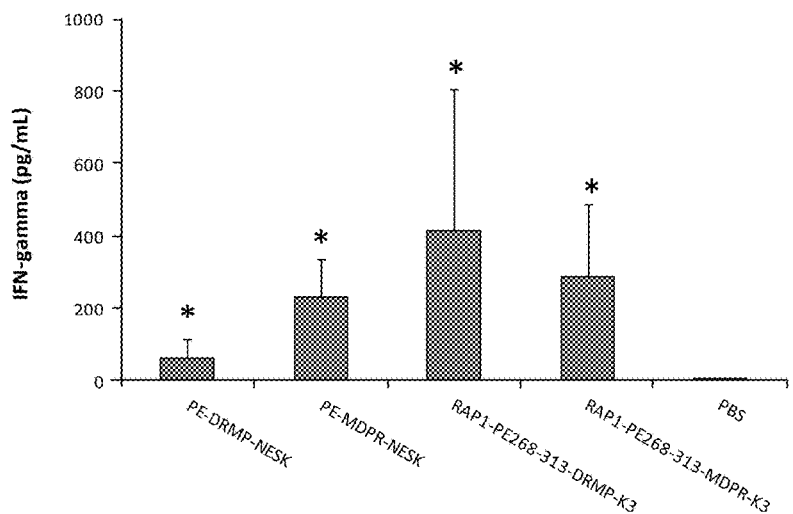
FIG. 7 is a graph showing IFN-γ secreted by PBMC from vaccinated swine after stimulation with respective PRRSV antigens.

FIG. 7 shows IFN-γ secreted by PBMC of vaccinated swine after stimulation. It was observed that vaccines comprising fusion antigens could induce higher IFN-γ secretion than placebo group.

Example 9

Viremia Studies in Swine

Five-weeks-old SPF swine (2-4 swine per group) were injected intramuscularly with one of the following vaccines: (1) PRRSFREE, (2) PE-DRMP-NESK, (3) PE-MDPR-NESK, (4) RAP1-PE$_{268-313}$-DRMP-K3, (5) RAP1-PE$_{268-313}$-MDPR-K3 in 2 ml of 50% ISA206, or (6) PBS as placebo, twice at weekly intervals. The antigen in each injection was 300 μg in 2 ml of 50% ISA206. The vaccinated swine were intranasally challenged with 2×10 TCID50 of PRRSV at three weeks after the last immunization. Blood sample were collected weekly. Viral RNA were extracted from the sera and quantified using one-step SyBR Green real-time PCR to determine the levels of viremia. The experimental results indicated that vaccines comprising fusion antigens could reduce the virus load.

Table 2 shows SEQ ID NOs. of peptides used for making various fusion proteins.

TABLE 2

| Component | SEQ ID NO: | Length |
|---|---|---|
| Minimum Pseudomonas exotoxin A (PE) binding domain 1a (APC-binding domain, a.a. 1-a.a. 252 of PE) | 1 | 252 |
| PE$_{253-313}$ (translocation domain) | 2 | 61 |
| PE$_{268-313}$ (translocation domain)* | 3 | 46 |
| PE$_4$ Core (PE translocation domain core; a.a. 280-a.a. 313 of PE) | 4 | 34 |
| PE$_{313}$ (a.a. 1-a.a. 313 of PE) | 5 | 313 |
| PE$_{253-364}$ (translocation domain) | 6 | 112 |
| PE$_{407}$ (a.a. 1-a.a. 407 of PE) | 7 | 407 |
| RAP1 Minimum (domain III of RAP1) | 8 | 104 |
| A2M Minimum | 9 | 153 |
| HIV-Tat Minimum | 10 | 24 |
| HSPs Minimum | 11 | 641 |
| NESK is LQKKLEELELAKDEL ** | 12 | 15 |
| NES consensus sequence is L$_{xx}$KL$_{xx}$L$_x$L$_x$, wherein "L" is leucine, "K" is lysine and "x" is any naturally occurring amino acid. | 13 | 11 |
| NES is LQKKLEELELA | 14 | 11 |
| KDEL (K) | 15 | 4 |
| KDELKDELKDEL (K3) | 16 | 12 |
| KKDLRDELKDEL (K3) | 17 | 12 |
| KKDELRDELKDEL (K3) | 18 | 13 |
| KKDELRVELKDEL (K3) | 19 | 13 |
| PCV2 ORF2 (truncated porcine circovirus type 2 ORF2; aa 42-aa 233) | 20 | 192 |
| Full length PE (Exotoxin A, Pseudomonas aeruginosa) | 21 | 613 |

TABLE 2-continued

| Component | SEQ ID NO: | Length |
|---|---|---|
| DGD (ORF7 antigen with a tandem repeat D) | 22 | 220 |
| D (ORF7 antigen without a tandem repeat D)<br>RHHFTPSERQLCLSSIQTAFNQGAGTCILSDSGRISYTVEFSLPTH<br>HTVRLIRVTAPPSA | 23 | 60 |
| R (RSAB) | 24 | 62 |
| M (M12)*** | 25 | 165 |
| P (PQAB)**** | 26 | 58 |
| $PE_{313}$--DRMP-NESK (or PE-DRMP-NESK) | 27 | 841 |
| $PE_{313}$-MDPR-NESK (or PE-MPDR-NESK) | 28 | 746 |
| RAP1-$PE_{268-313}$-DRMP-K3 | 29 | 677 |
| RAP1-$PE_{268-313}$-MDPR-K3 | 30 | 584 |
| $PE_{313}$-PCV2-NESK (or PE-PCV2-NESK) | 31 | 525 |
| PE1-267 (PE binding domain) | 32 | 267 |
| Alternative D (ORF7 antigen, without a tandem repeat D)<br>HHFTPSERQLCLSSIQTAFNQGAGTCILSDSGRISYTVEFSLPTHH<br>TVRLIRVTAPPSA | 33 | 59 |
| N-terminal portion of ORF6 [from a PRRSV isolate in Taiwan]<br>GSSLDDFCYDSTAPQKVLLAFSITY | 34 | 25 |
| N-terminal portion of ORF5 [from a PRRSV isolate in Taiwan]<br>ASNDSSSHLQLIYNLTLCELNGTDWLANKFDWA | 35 | 33 |
| N-terminal portion of ORF6<br>MGSLDDFCNDSTAAQKLVLAFSTYTPI | 36 | 28 |
| N-terminal portion of ORF5<br>FVAGGSSSTYQYIYNLTICELNGTDWLSNHFDWA | 37 | 34 |
| PRRSV ORF5, Type 1 (European) PRRSV strain Accession No. CAA63493.1<br>MRCSHKLGRFLTPHSCFWWLFLLCTGLSWSFVAGGSSSTYQYI<br>YNLTICELNGTDWLSNHFDWAVETFVL<br>YPVATHILSLGFLTTSHFFDALGLGAVSTIGFVGGRYVLSSVYG<br>ACAFAAFVCFVIRAVKNCMAFRYAHT<br>RFTNFIVDDRGIHRWKSPIVVEKLGKAEVGGDLVTIKHVVLEG<br>VKAQPLTRTSAEQWEA | 38 | 200 |
| PRRSV ORF6 Type 1 (European) PRRSV strain, Accession No. CAA63494.1<br>MGSLDDFCNDSTAAQKLVLAFSITYTPIMIYALKVSRGRLLGL<br>LHILIFLNCSFTFGYMTYVRFQSTNRV<br>ALTLGAVVALLWGVYSFTESWKFVTSRCRLCCLGRRYILAPAH<br>HVESAAGLHSIPASGNRAYAVRKPGLT<br>SVNGTLVPGLRSLVLGGKRAVKRGVVNLVKYGR | 39 | 173 |
| PRRSV ORF5, Type 2 (North America) PRRSV strain, Accession number of ORF5: AKS03861.1<br>MLGKCLTAGCCSRLLFLWCTVPSCFVALVGASNSSSSYSQLIY<br>NLTLCELNGTDWLANKFDWAVETFVIF<br>PVLTHIVSYGALTTSHFLDTVGLITVSTAGFYHGRYVLSSIYATC<br>ALAALICFVIRLAKNCMSWRYSCTR<br>YTNFLLDTKGRIYRWRSPVIIEKGGKVEVEGHLIDLKRVVLDGS<br>AATPVTKISAEQWGRP | 40 | 200 |

TABLE 2-continued

| Component | SEQ ID NO: | Length |
|---|---|---|
| PRRSV ORF6: Type 2 (North America) PRRSV strain, Accession No. AKS03862.1<br>M<u>GSSLDDFCHDSTAPQKVILAFSITY</u>TPVMIYALKVSRGRLLG<br>LLHLLIFLNCAFTFGYMTFVHFQSTNR<br>VALTMGAVVALLWGVYSAIETWRFITSRCRLCLLGRKYILAPA<br>HHVESAAGFHPIAASDNHAFVVRRPGS<br>TTVNGTLVPGLKSLVLGGRKAVKQGVVNLVKYAK | 41 | 174 |

*: PE$_{268-313}$ is a.a. 268-a.a. 313 of full length PE; PE$_{313}$ is a.a. 1-a.a. 31 of full length PE; PE$_{407}$ is a.a. 1-a.a. 407 of full length PE.
**: The bold letters represents the ammo acid sequence of an artificial nuclear exporting signal; the underlined letters represents the amino acid sequence of an endoplasmic reticulum retention signal.
***: M (M12) is a fusion polypeptide prepared by fusion of PRRSV NSP 10 (C-terminal domain sequence) and NSP 11 (N-terminal domain sequence). That is, the polypeptide is derived from the nonstructural proteins ORF1b NSP 10 C-terminal portion and NSP 11 N-terminal portion.)
****: P (PQAB) is a polypeptide prepared by fusion of PRRSV ORF6 a.a. 2 -a.a. 26 and ORF5 aa 31-aa 63. See U.S. Pat. No. 7465455. The sequence in regular letters derives from PRRSV ORF6/matrix protein sequence, and the sequence in bold letters derives from PRRSV ORF 5 sequence. The major envelope protein ((GP5) encoded by the ORF5 of PRRSV has a critical role in inducing virus neutralizing (VN) antibody and cross protection among different strains of PRRSV. Since there are sequence variations among different strains, the sequences herein are disclosed for illustration purpose.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the appended claims.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A fusion protein comprising:
   (a) an antigen-presenting cell (APC)-binding domain located at the N-terminus of the fusion protein, wherein the APC-binding domain is a *Pseudomonas* exotoxin A (PE) binding domain;
   (b) a translocation peptide of 34-112 amino acid residues in length, comprising the amino acid sequence of SEQ ID NO: 4, 2, 3, or 6, located at the C-terminus of the APC-binding domain;
   (c) a fusion antigen comprising:
      (i) a porcine reproductive and respiratory syndrome virus (PRRSV) ORF7 antigen;
      (ii) a PRRSV ORF1b antigen;
      (iii) a PRRSV ORF6 antigen; and
      (iv) a PRRSV ORF5 antigen;
   (d) a nuclear export signal comprising the amino acid sequence of SEQ ID NO: 13, located at the C-terminus of the fusion antigen or between the translocation peptide and the fusion antigen;
   wherein the fusion antigen does not comprise full-length ORF7, ORF6, ORF5, and ORF1b protein sequences; and
   (e) an endoplasmic reticulum retention sequence, located at the C-terminus of the fusion antigen when the nuclear export signal is located at between the translocation peptide and the fusion antigen, or located at the C-terminus of the nuclear export signal when the nuclear export signal is located at the C-terminus of the fusion antigen.

2. The fusion protein of claim 1, wherein the ORF7 or ORF1b antigen is located N-terminal to the ORF6 antigen, and the ORF5 antigen is located C-terminal to the ORF6 antigen.

3. The fusion protein of claim 1, wherein the fusion antigen comprises two tandem repeats of the ORF7 antigen.

4. The fusion protein of claim 1, wherein the ORF5 antigen is located C-terminal to the ORF6 antigen.

5. The fusion protein of claim 1, wherein the ORF6 antigen comprises the N-terminal portion amino acid sequence of the PRRSV ORF6 and the ORF5 antigen comprises the N-terminal portion amino acid sequence of the PRRSV ORF5, and the fusion antigen does not comprise the C-terminal portion amino acid sequences of the ORF6 and ORF5.

6. The fusion protein of claim 5, wherein the ORF6 antigen is located N-terminal to the ORF5 antigen without a bridge or a linker between the ORF6 and ORF5 antigens.

7. The fusion protein of claim 5, wherein the ORF1b antigen comprises the C-terminal portion amino acid sequence of ORF1b NSP 10 and the N-terminal portion amino acid sequence of ORF1b NSP 11, and the fusion antigen is devoid of the N-terminal and C-terminal portion amino acid sequences of the ORF1b.

8. The fusion protein of claim 1, wherein the translocation peptide has 34-61 amino acid residues in length.

9. The fusion protein of claim 1, wherein the endoplasmic reticulum retention sequence comprises the amino acid sequence KDEL (SEQ ID NO: 15) without a tandem repeat of the amino acids KDEL.

10. The fusion protein of claim 1, wherein the nuclear export signal and the ER retention sequence forms a fusion peptide with the amino acid sequence of SEQ ID NO: 12.

11. A composition comprising:
 (i) the fusion protein of claim 1; and
 (ii) a porcine circovius type 2 (PCV2) fusion protein, comprising:
  (a) an antigen-presenting cell (APC)-binding domain or a CD91 receptor-binding domain, located at the N-terminus of the fusion protein;
  (b) a translocation peptide of 34-112 amino acid residues in length, comprising the amino acid sequence of SEQ ID NO: 4, 2, 3, or 6, located at the C-terminus of the APC-binding domain or the CD91 receptor-binding domain;
  (c) a PCV2 ORF2 antigen;
  (d) a nuclear export signal comprising the amino acid sequence of SEQ ID NO: 13, located at the C-terminus of the PCV2 ORF2 antigen or between the translocation peptide and the PCV2 ORF2 antigen; and
  (e) an endoplasmic reticulum retention sequence, located at the C-terminus of the PCV2 fusion protein when the nuclear export signal is located between the translocation peptide and the PCV2 ORF2 antigen, or located at the C-terminus of the nuclear export signal when the nuclear export signal is located at the C-terminus of the PCV2 ORF2 antigen;

wherein the PCV2 ORF2 antigen comprises the C-terminal portion amino acid sequence of PCV2 ORF 2 protein, and the PCV2 fusion protein does not comprise the N-terminal portion amino acid sequence of the PCV2 ORF2 protein.

12. The fusion protein of claim 1, wherein the translocation peptide has 34-46 amino acid residues in length.

13. The fusion protein of claim 1, wherein the fusion antigen comprises:
 (i) the amino acid sequence of SEQ ID NO: 22, 23 or 33;
 (ii) the amino acid sequence of SEQ ID NO: 24;
 (iii) the amino acid sequence of SEQ ID NO: 25; and
 (iv) the amino acid sequence of SEQ ID NO: 26.

14. A method for inducing antigen-specific cell-mediated and humoral responses, comprising:
 administering a composition comprising a therapeutically effective amount of the fusion protein of claim 1 to a subject in need thereof, and thereby inducing antigen-specific cell-mediated and humoral responses.

15. A method for inducing antigen-specific cell-mediated and humoral responses, comprising:
 administering the composition of claim 11 to a subject in need thereof, and thereby inducing antigen-specific cell-mediated and humoral responses.

16. The fusion protein of claim 1, wherein the fusion protein comprises the amino acid sequence of SEQ ID NO: 27 or 28.

17. The fusion protein of claim 1, wherein the *Pseudomonas* exotoxin A (PE) binding domain comprises the amino acid sequence of SEQ ID NO: 1 or 32.

18. A composition comprising:
 (a) the fusion protein of claim 17; and
 (b) a porcine circovius type 2 (PCV2) fusion protein comprising the amino acid sequence of SEQ ID NO: 31.

19. A method for inducing antigen-specific cell-mediated and humoral responses, comprising:
 administering a composition comprising a therapeutically effective amount of the fusion protein of claim 12 to a subject in need thereof, and thereby inducing antigen-specific cell-mediated and humoral responses.

20. A method for inducing antigen-specific cell-mediated and humoral responses, comprising:
 administering a composition comprising a therapeutically effective amount of the fusion protein of claim 13 to a subject in need thereof, and thereby inducing antigen-specific cell-mediated and humoral responses.

* * * * *